(12) United States Patent
Burkholz et al.

(10) Patent No.: US 12,427,287 B2
(45) Date of Patent: Sep. 30, 2025

(54) VASCULAR ACCESS INSTRUMENT HAVING A FLUID PERMEABLE STRUCTURE, AND RELATED DEVICES AND METHODS

(71) Applicant: Becton, Dickinson and Company, Franklin Lakes, NJ (US)

(72) Inventors: Jonathan Karl Burkholz, Salt Lake City, UT (US); Daniel Blanchard, Bountiful, UT (US); Curtis H. Blanchard, Herriman, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 514 days.

(21) Appl. No.: 17/983,886

(22) Filed: Nov. 9, 2022

(65) Prior Publication Data
US 2023/0064113 A1 Mar. 2, 2023

Related U.S. Application Data

(63) Continuation of application No. 16/838,831, filed on Apr. 2, 2020, now Pat. No. 11,504,503.
(Continued)

(51) Int. Cl.
*A61M 25/06* (2006.01)
*A61M 25/02* (2006.01)
*A61M 25/09* (2006.01)

(52) U.S. Cl.
CPC ........ *A61M 25/0606* (2013.01); *A61M 25/02* (2013.01); *A61M 25/0625* (2013.01); *A61M 25/09* (2013.01); *A61M 2025/09083* (2013.01)

(58) Field of Classification Search
CPC .... A61M 25/0606; A61M 2025/09083; A61M 2025/09091; A61M 25/09;
(Continued)

(56) References Cited

U.S. PATENT DOCUMENTS

| 4,464,171 A | 8/1984 | Garwin |
| 4,748,986 A | 6/1988 | Morrison et al. |

(Continued)

FOREIGN PATENT DOCUMENTS

| EP | 0611073 A1 | 8/1994 |
| EP | 1266670 A1 | 12/2002 |

(Continued)

*Primary Examiner* — Phillip A Gray
(74) *Attorney, Agent, or Firm* — The Webb Law Firm

(57) ABSTRACT

A delivery device to deliver a guidewire through an intravenous catheter assembly may include a housing, which may include a distal end, a proximal end, and a slot. The delivery device may include a guidewire, which may include a proximal end and a distal end. The delivery device may include a guidewire hub disposed within the housing. The guidewire may be secured to the guidewire hub, and the guidewire hub may be configured to move along the slot to advance the guidewire in a distal direction. The distal end of the guidewire may include a fluid permeable structure. For example, the fluid permeable structure may include an elongated core and a coil extending around the elongated core. In some embodiments, a space between the elongated core and the coil may be configured to receive blood in response to the guidewire being inserted into the vasculature.

20 Claims, 22 Drawing Sheets

Related U.S. Application Data

(60) Provisional application No. 62/830,286, filed on Apr. 5, 2019.

(58) Field of Classification Search
CPC .............. A61M 25/0625; A61M 25/02; A61M 2025/09175; A61M 25/09041
USPC ................................................... 604/164.13
See application file for complete search history.

(56) References Cited

U.S. PATENT DOCUMENTS

| | | | |
|---|---|---|---|
| 5,107,852 A | 4/1992 | Davidson et al. | |
| 5,865,768 A | 2/1999 | Orr | |
| 6,132,388 A * | 10/2000 | Fleming | A61M 25/09 600/585 |
| 6,390,992 B1 | 5/2002 | Morris et al. | |
| 6,648,837 B2 | 11/2003 | Kato et al. | |
| 2002/0198468 A1 | 12/2002 | Kato et al. | |
| 2010/0210934 A1* | 8/2010 | Belson | A61B 5/150503 600/371 |
| 2012/0238872 A1 | 9/2012 | Schwager | |
| 2012/0283700 A1 | 11/2012 | Pawluck | |
| 2014/0094774 A1 | 4/2014 | Blanchard | |
| 2015/0231364 A1 | 8/2015 | Blanchard et al. | |
| 2016/0045715 A1 | 2/2016 | Galgano et al. | |
| 2016/0067453 A1 | 3/2016 | Braithwaite et al. | |
| 2016/0256667 A1* | 9/2016 | Ribelin | A61M 25/09041 |
| 2018/0133437 A1 | 5/2018 | Blanchard | |
| 2019/0021640 A1 | 1/2019 | Burkholz et al. | |

FOREIGN PATENT DOCUMENTS

| | | |
|---|---|---|
| JP | 2001178829 A | 7/2001 |
| JP | 2001519215 A | 10/2001 |
| JP | 2015506777 A | 3/2015 |
| JP | 2016221231 A | 12/2016 |
| WO | 2013019947 A2 | 2/2013 |

* cited by examiner

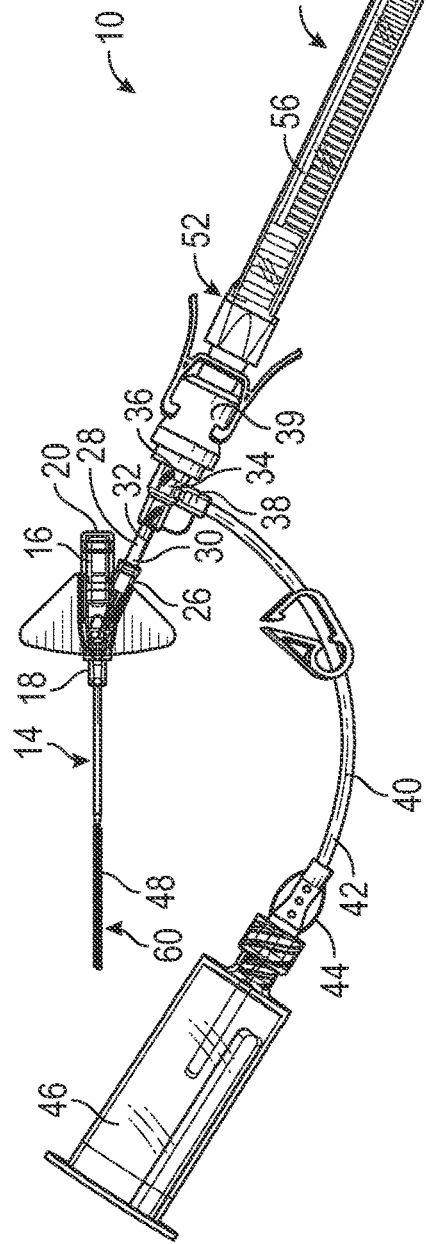
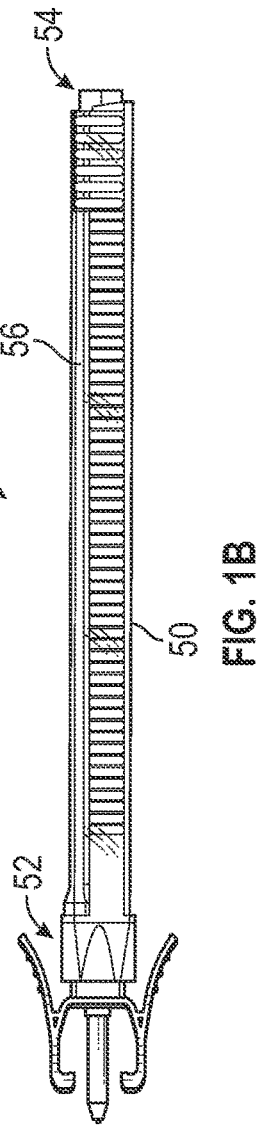
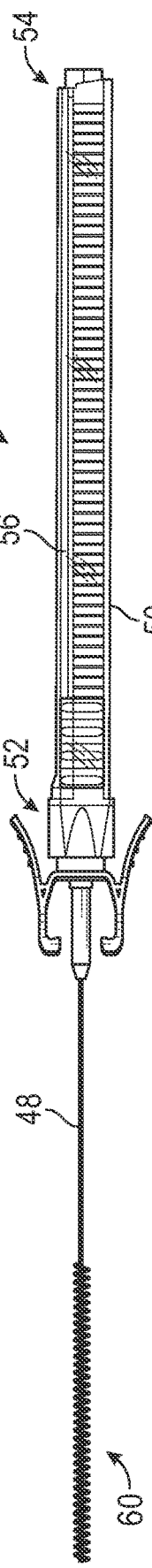
FIG. 1A
FIG. 1B
FIG. 1C

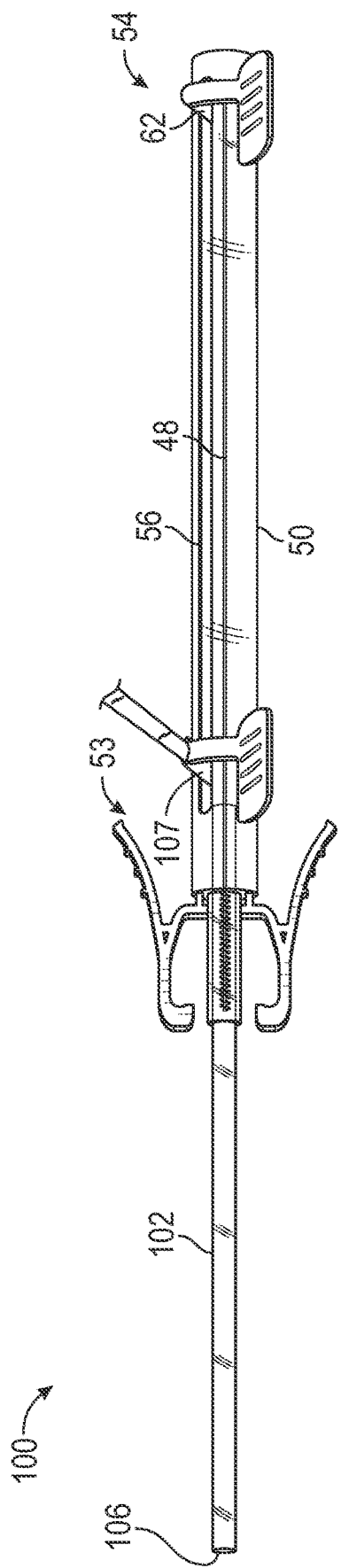
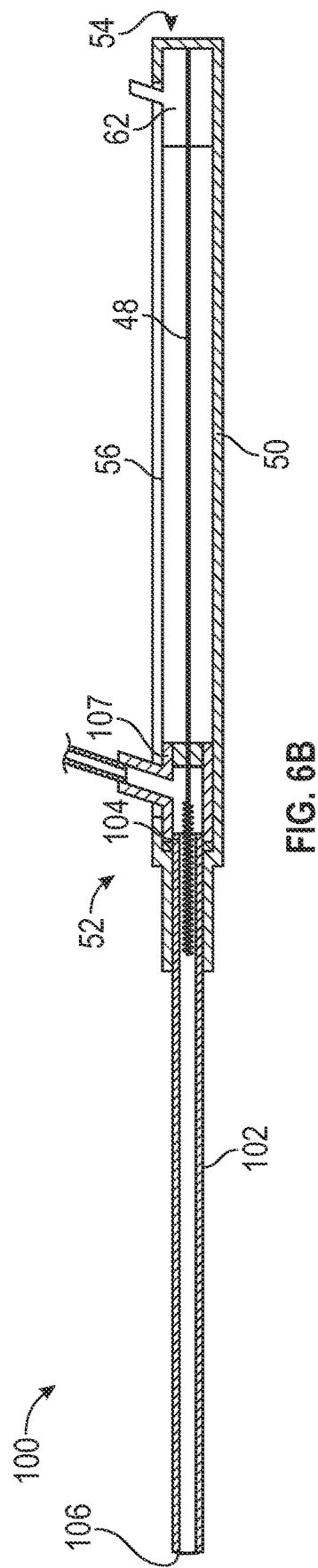
FIG. 6A
FIG. 6B

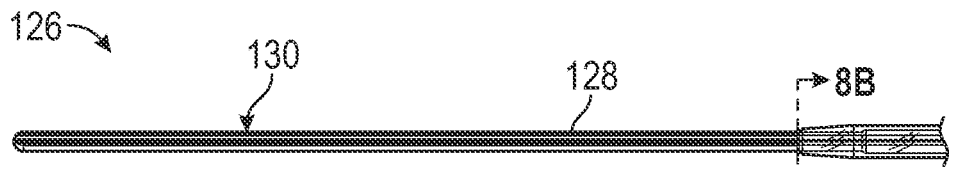
FIG. 8A  FIG. 8B

FIG. 8C  FIG. 8D
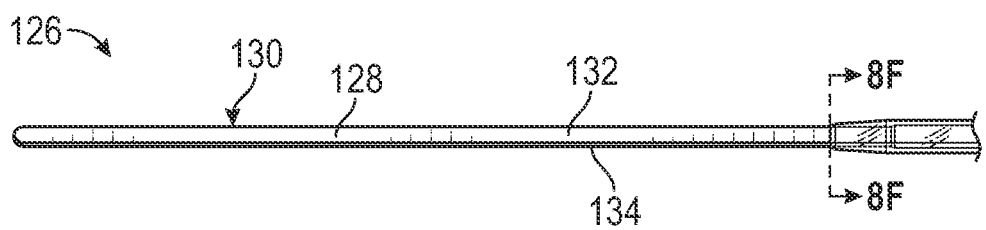
FIG. 8E  FIG. 8F
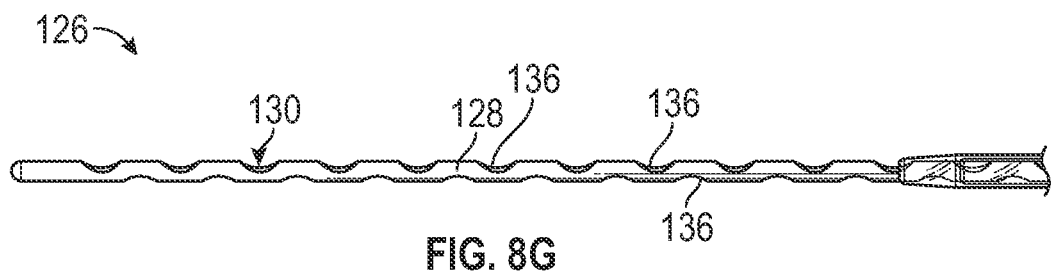
FIG. 8G
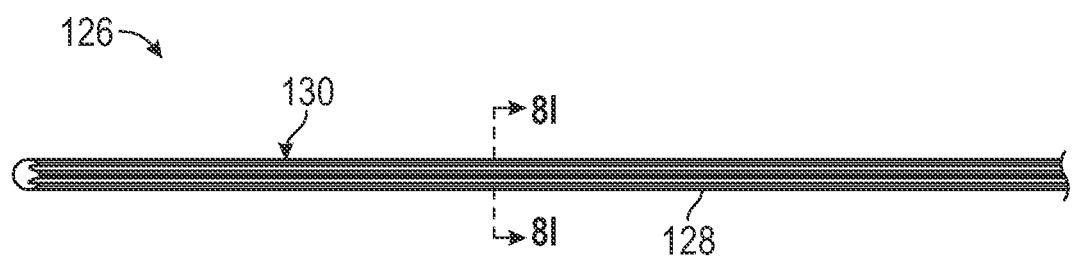
FIG. 8H

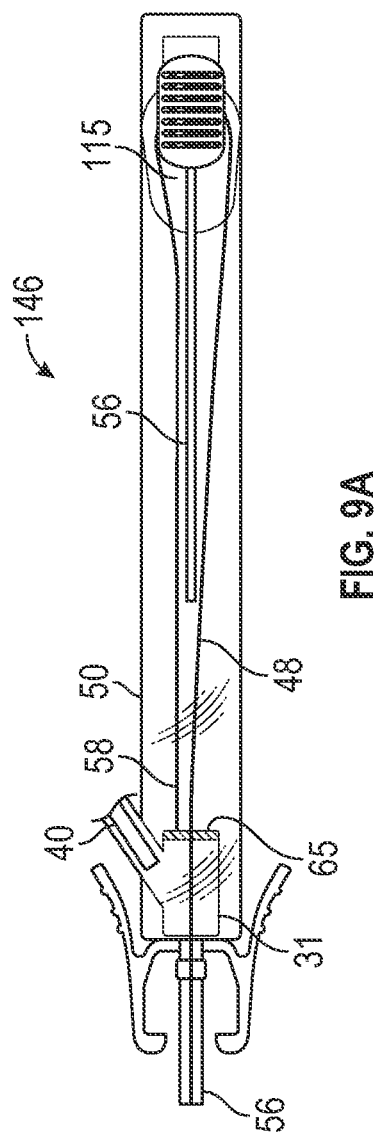
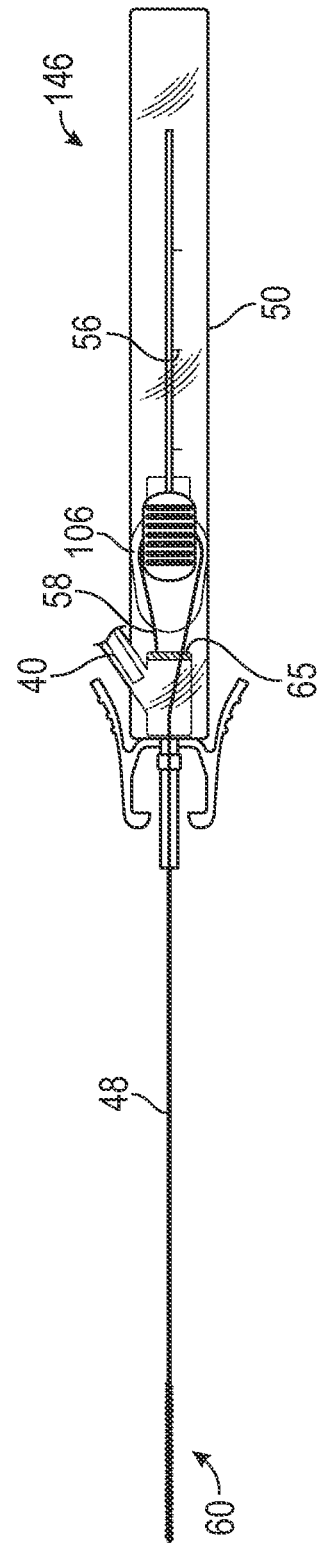
FIG. 9A
FIG. 9B

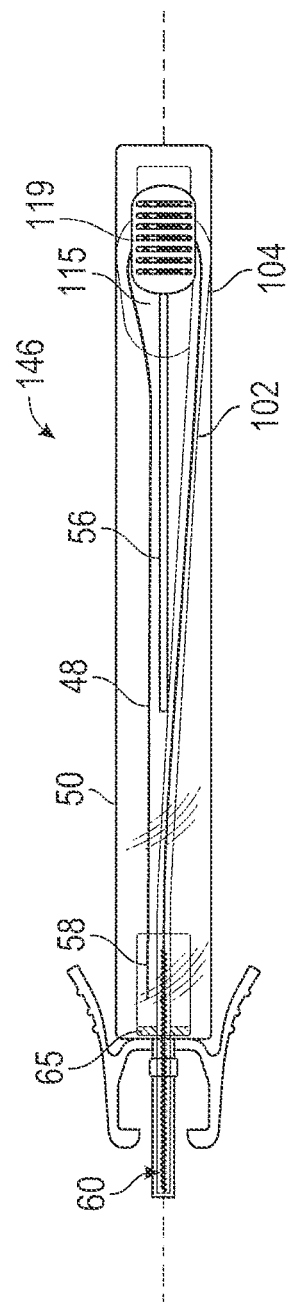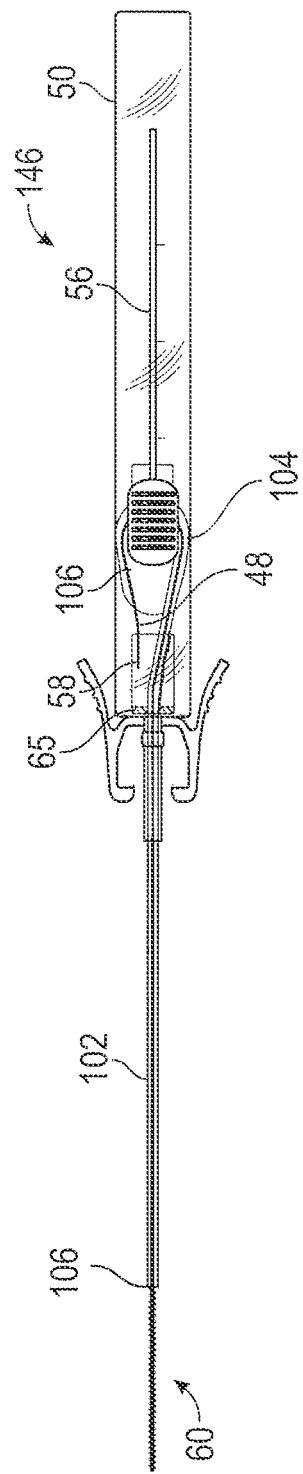

VASCULAR ACCESS INSTRUMENT HAVING A FLUID PERMEABLE STRUCTURE, AND RELATED DEVICES AND METHODS

CROSS-REFERENCE TO RELATED APPLICATIONS

This application is a continuation of U.S. application Ser. No. 16/838,831, filed Apr. 2, 2020, entitled "Vascular Access Instrument Having a Fluid Permeable Structure, and Related Devices and Methods", which claims the benefit of U.S. Provisional Application No. 62/830,286, filed Apr. 5, 2019, and entitled "Vascular Access Instrument Having a Fluid Permeable Structure, and Related Devices and Methods", the disclosures of which are incorporated herein by reference in their entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). A vascular access device may be used for continuous infusion therapy or for intermittent therapy.

A common type vascular access device is an over-the-needle peripheral intravenous catheter (PIVC). As its name implies, the "over-the-needle" PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient. Once placement of the needle within the vasculature has been confirmed, the clinician may temporarily occlude flow in the vasculature and withdraw the needle, leaving the PIVC in place for future fluid infusion and/or blood withdrawal.

Currently, there may be several limitations to the use of a PIVC for fluid infusion or blood draw. The PIVC or vein may narrow, collapse, or clog with time, leading to failure of the PIVC. Also, blood extracted from PIVCs may often need to be discarded due to concerns regarding sample quality, which may result in an unusable sample and a need to repeat blood collection. Further, use of a PIVC to draw blood can be slow and somewhat inefficient, particularly when the patient as difficult intravenous access or veins that are not readily accessed by the clinician.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems, devices, and methods. More particularly, in some embodiments, the present disclosure relates to systems, devices, and methods for placing an instrument through a catheter, which may be indwelling. In some embodiments, the instrument may include a guidewire. In some embodiments, the catheter may include a PIVC, a midline catheter, or a peripherally inserted central catheter (PICC).

In some embodiments, the instrument may extend beyond a distal end or tip of the catheter, which may move or push away anything within vasculature of a patient that might otherwise occlude the catheter during a blood draw. For example, the instrument may move or push away fibrin material, thrombosis, or even a vein wall. In some embodiments, the instrument may push open a valve within the vasculature, allowing backflow of blood into the catheter. In some embodiments, the instrument may open the distal tip of the catheter. In some embodiments, the instrument may reduce kinking of the catheter and flow restriction due to kinking of the catheter. In some embodiments, the instrument may extend beyond the distal tip of the catheter and an insertion site of the catheter, which may facilitate bypass of localized vein diameter restriction due to thrombus and/or vein construction. In some embodiments, the instrument may move the distal tip of the catheter toward a center of the vein, away from the vein wall, which may reduce opportunity for occlusion and/or damage to the vein wall from shear stress due to flow.

In some embodiments, the instrument may include a fluid permeable structure, which may provide a long, narrow inlet path or multiple inlet paths into the distal tip of the catheter. In some embodiments, the fluid permeable structure may prevent fibrin material, thrombosis, or another material from obstructing the distal tip of the catheter. In some embodiments, the instrument may increase dwell time of the catheter. In some embodiments, the instrument may allow the catheter to be constructed of a softer and/or more flexible material, which may be gentler on the vasculature. In some embodiments, the instrument may allow blood to enter the catheter from a longer portion of a vein and may reduce blood collection fill time, especially for small gauge catheters.

In some embodiments, the guidewire may be delivered through an intravenous catheter assembly via any suitable delivery device. In some embodiments, a delivery device to deliver the guidewire through an intravenous catheter assembly may include a housing, which may include a distal end, a proximal end, and a slot. In some embodiments, the delivery device may include the guidewire, which may include a proximal end and a distal end. In some embodiments, the distal end of the guidewire may include the fluid permeable structure.

In some embodiments, the delivery device may include a guidewire hub, which may be disposed within the housing. In some embodiments, the guidewire may be secured to the guidewire hub. In some embodiments, the guidewire hub may be configured to move along the slot to advance the guidewire in a distal direction and distal to the distal end of the housing. In some embodiments, the guidewire may be advanced in a distal direction and/or retracted in a proximal direction.

In some embodiments, the fluid permeable structure may include an elongated core and a coil extending around the elongated core. In some embodiments, the coil may be coupled to the elongated core. In some embodiments, blood may flow within a space between the elongated core and the coil in response to the guidewire being inserted into the vasculature. In some embodiments, the delivery device may include a gap between an outer diameter of the guidewire and an inner diameter of the catheter, which may allow blood to flow proximally through gap from the vasculature.

In some embodiments, the guidewire may include a rounded distal tip, which may reduce a risk of damage to the vasculature when the guidewire is inserted into the vasculature. In some embodiments, the rounded distal tip may reduce a risk of thrombus development or other complications. In some embodiments, the rounded distal tip may be spot welded, an adhesive, or formed via another suitable means. In some embodiments, the rounded distal tip may be constructed of metal, plastic, an elastomer, or another suitable material.

In some embodiments, the coil may be fixed to the elongated core at one or more positions along a length of the elongated core. For example, one or more bridges may extend from the coil to the elongated core to secure the coil to the elongated core. In some embodiments, the distal end of the coil may be coupled to the elongated core via the rounded distal tip. In further detail, in some embodiments, a distal end of the coil may be directly coupled to the rounded distal tip, which may be directly coupled to the elongated core.

In some embodiments, the coil may be tightly wound around the elongated core at one or more locations to couple the coil to the elongated core. In some embodiments, the coil may include the distal end and a proximal end. In some embodiments, the distal end of the coil and/or the proximal end of the coil may be tightly wound around the elongated core. In some embodiments, the elongated core may include a first portion, which may include a first outer diameter, and a second portion, which may include a second outer diameter. In some embodiments, the second outer diameter may be greater than the first outer diameter. In some embodiments, the coil may be tightly wound around the second portion.

In some embodiments, spacing between rings of the coil may be generally uniform. In some embodiments, the spacing between rings of the coil may vary. In some embodiments, along one or more portions of the coil, the spacing of the rings may be tight. For example, the rings may contact each other or be close to each other. In some embodiments, along other portions of the coil, the spacing of the rings may be more spread apart than along the portions of the coil. In some embodiments, the distal end of the coil may be disposed distal to the distal end of the elongated core. In these and other embodiments, the distal end of the coil may be open or closed.

In some embodiments, the delivery device may include tubing, which may include a proximal end and a distal end. In some embodiments, the guidewire may be delivered through the catheter assembly via any suitable delivery device. In some embodiments, the tubing may be configured to extend into the catheter and/or into the vasculature of a patient. In some embodiments, the guidewire may be disposed within the tubing. In some embodiments, the distal end of the tubing may include a fluid permeable structure. In some embodiments, the guidewire and/or the tubing may reduce a number of needle sticks that a patient experiences as the catheter may be replaced less frequently. In some embodiments, the tubing may allow a user to draw a blood sample or infuse fluid through the catheter when the catheter is no longer functional or less effective due to, for example, debris build up on the distal end of the catheter or collapse of the catheter.

In some embodiments, the delivery device may include a tubing hub disposed within the housing. In some embodiments, the tubing may be secured to the tubing hub. In some embodiments, the tubing hub may be configured to move along the slot to advance the tubing in a distal direction distal to the distal end of the housing. In some embodiments, the tubing may be advanced in the distal direction and/or retracted in the proximal direction any number of times.

In some embodiments, a catheter system may include the delivery device and the catheter assembly. In some embodiments, the catheter assembly may include a catheter adapter, which may include a distal end, a proximal end, a lumen extending between the distal end and the proximal end. In some embodiments, the catheter may be secured to the catheter adapter and may extend distally from the catheter adapter. In some embodiments, the catheter may include one or more diffuser holes, which may provide additional paths for blood to enter the catheter.

In some embodiments, the catheter adapter may include a side port, which may be angled with respect to the distal end of the catheter adapter. In some embodiments, the catheter system may include an extension tube, which may include a distal end and a proximal end. In some embodiments, the distal end of the extension tube may be coupled to the side port. In some embodiments, the distal end of the extension tube may be integrated with the side port. In some embodiments, the fluid permeable structure may facilitate entry of blood into the catheter in response to a negative pressure being applied to the side port of the catheter adapter.

In some embodiments, a connector may be coupled to the proximal end of the extension tube. In some embodiments, the proximal end of the extension tube may be integrated with the connector. In some embodiments, the connector may include a first port and a second port. In some embodiments, the connector may include more than two ports. In some embodiments, the delivery device may be coupled to the first port of the connector. In some embodiments, another extension tube may be coupled to the second port of the connector. In some embodiments, a blood collection device may be coupled to a proximal end of the other extension tube.

In some embodiments, blood may be prevented from entering the delivery device. For example, the distal end of the housing may include a septum to prevent fluid from flowing into the distal end of the housing. In some embodiments, a fluid pathway of the catheter system may include one or more of the following: the catheter, the catheter adapter, the extension tube, and the other extension tube. In some embodiments, blood may be collected via the fluid pathway, which may not extend through the housing of the delivery device. In some embodiments, the fluid pathway may not include or be disposed within a majority of or an entirety of the housing. In some embodiments, blood may not flow within or through the housing of the delivery device. In some embodiments, the delivery device may not be a blood collection device; instead, the delivery device may facilitate blood flow through the catheter and allow collection of blood through the fluid pathway, which may include the catheter assembly and/or may not include the housing of the delivery device.

In some embodiments, the delivery device may be coupled to the proximal end of the catheter adapter. In these embodiments, the fluid pathway of the catheter system may include the catheter, the catheter adapter, and the extension tube. In some embodiments, the blood collection device may be coupled to the proximal end of the extension tube.

In some embodiments, an instrument of the catheter system may include an extension device, which may include an elongated body. In some embodiments, the extension device may be obturator-like except that the extension device may not block the fluid pathway through the catheter; instead the extension device may facilitate fluid flow through the catheter. In some embodiments, the elongated body may include a fluid permeable structure that may be configured to allow fluid to enter the distal end of the catheter in response to the extension device being inserted through the catheter. In some embodiments, the fluid permeable structure of the extension device may include one or more grooves, one or more flat regions, one or more side holes, or one or more axially running channels. In some embodiments, the extension device may include a rod that includes one or more grooves, one or more flat regions, one or more side holes, or one or more axially running channels.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is an upper perspective view of an example catheter system, according to some embodiments;

FIG. 1B is an upper perspective view of an example delivery device of the catheter system of FIG. 1A, illustrating an example guidewire in a retracted position, according to some embodiments;

FIG. 1C is an upper perspective view of the delivery device of the catheter system of FIG. 1A, illustrating the guidewire in an advanced position, according to some embodiments;

FIG. 6A is an upper perspective view of another delivery device that may be used with the catheter system of FIG. 1A, according to some embodiments;

FIG. 6B is a cross-sectional view of the other delivery device of FIG. 6A, according to some embodiments;

FIG. 8A is an upper perspective view of an example distal end of an example extension device, according to some embodiments;

FIG. 8B is a cross-sectional view of the distal end along the line 8B-8B of FIG. 8A, according to some embodiments;

FIG. 8C is an upper perspective view of another example distal end of the extension device of FIG. 8A, according to some embodiments;

FIG. 8D is a cross-sectional view of the other distal end along the line 8D-8D of FIG. 8C, according to some embodiments;

FIG. 8E is an upper perspective view of another example distal end of the extension device of FIG. 8A, according to some embodiments;

FIG. 8F is a cross-sectional view of the other distal end along the line 8F-8F of FIG. 8E, according to some embodiments;

FIG. 8G is an upper perspective view of another example distal end of the extension device of FIG. 8A, according to some embodiments;

FIG. 8H is an upper perspective view of another example distal end of the extension device of FIG. 8A, according to some embodiments;

FIG. 9A is an upper perspective view of another delivery device, illustrating the guidewire in a retracted position, according to some embodiments;

FIG. 9B is an upper perspective view of the delivery device of FIG. 9A, illustrating the guidewire in an advanced position, according to some embodiments;

FIG. 10A an upper perspective view of another delivery device, illustrating the guidewire and example tubing in a retracted position, according to some embodiments;

FIG. 10B is an upper perspective view of the delivery device of FIG. 10A, illustrating the guidewire and example tubing an advanced position, according to some embodiments.

DESCRIPTION OF EMBODIMENTS

Figure 1D:
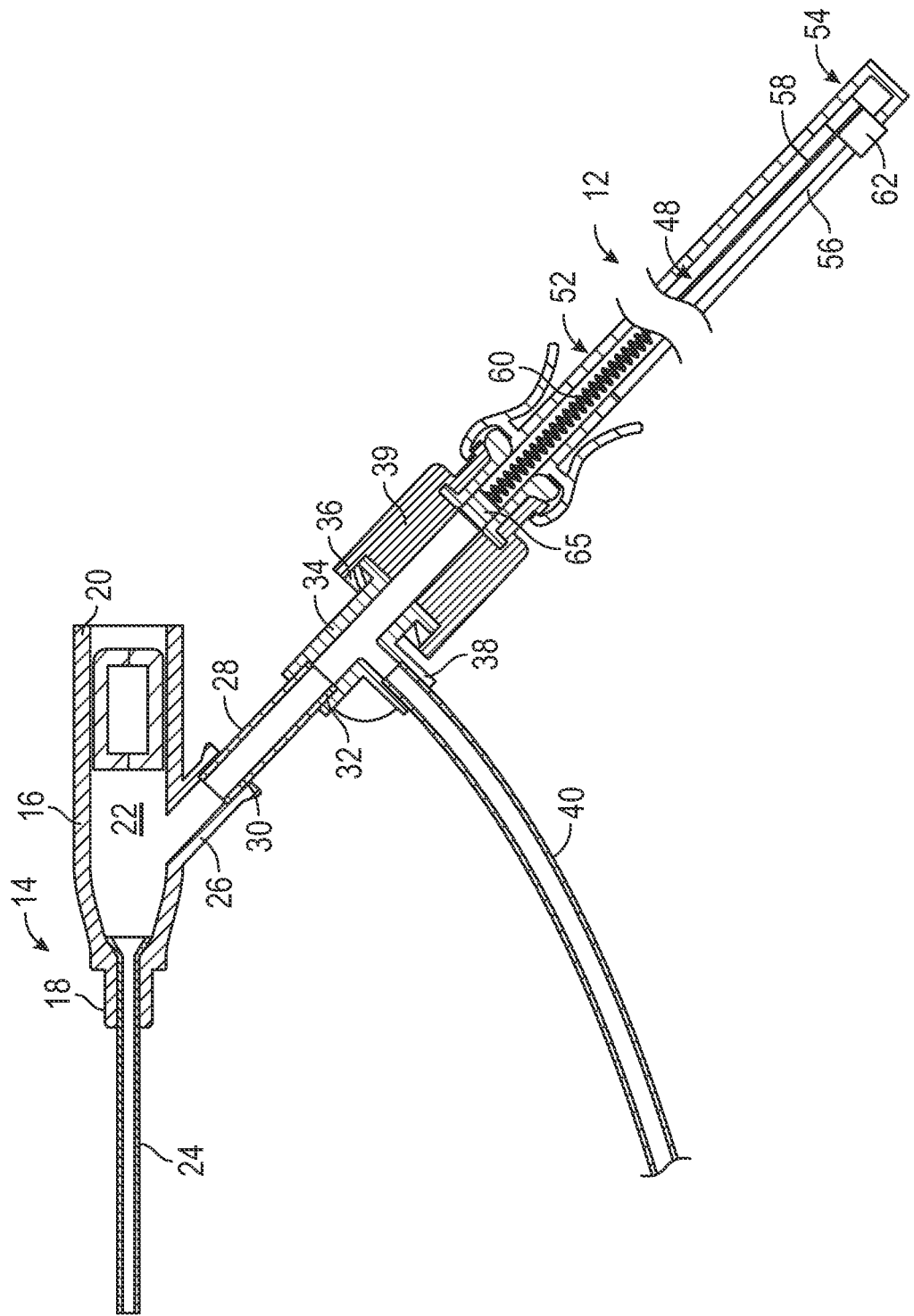
FIG. 1D is a cross-sectional view of the delivery device of the catheter system of FIG. 1A, illustrating the guidewire in the retracted position, according to some embodiments.
Figure 1E:
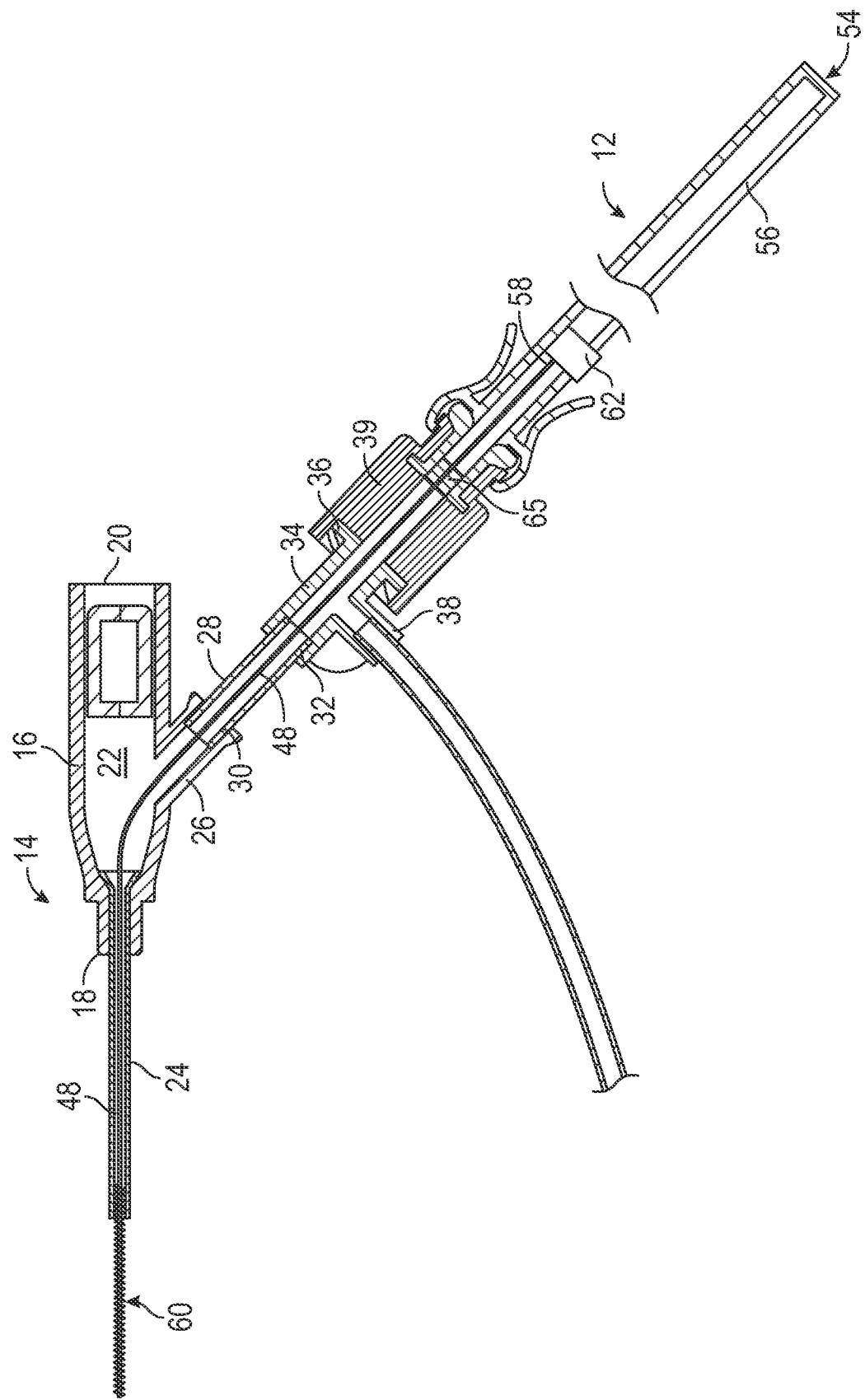
FIG. 1E is a cross-sectional view of the delivery device of the catheter system of FIG. 1A, illustrating the guidewire in the advanced position, according to some embodiments.

As used in the present disclosure, the term "distal" refers to a portion of a catheter system or component thereof that is farther from a user, and the term "proximal" refers to a portion of a catheter system or component thereof that is closer to the user. As used in the present disclosure, the term "user" may refer to a clinician, doctor, nurse, or any other care provider and may include support personnel.

Referring now to FIGS. 1A-1E, in some embodiments, a catheter system 10 may include a delivery device 12 and a catheter assembly 14. In some embodiments, the delivery device 12 may include any suitable delivery device, which may include any suitable housing. In some embodiments, the housing may include a collapsible tube or a flexible tube or any other suitable element that generally surrounds the instrument to facilitate a sterile environment. For example, the delivery device 12 may include a linear or rotary mechanism or any other suitable mechanism. In some embodiments, the delivery device 12 may be described, for example, in U.S. Patent Application 62/660,661, filed Apr. 20, 2018 entitled "INSTRUMENT DELIVERY DEVICE HAVING A ROTARY ELEMENT," U.S. Patent Application No. 62/773,029, filed Nov. 29, 2018, entitled "SYRINGE-BASED DELIVERY DEVICE FOR A VASCULAR ACCESS INSTRUMENT," and U.S. Patent Application No. 62/696,229, filed Jul. 10, 2018, entitled "DELIVERY DEVICE FOR A VASCULAR ACCESS INSTRUMENT," each of which is incorporated by reference in its entirety.

In some embodiments, the catheter assembly 14 may include a catheter adapter 16, which may include a distal end 18, a proximal end 20, a lumen 22 extending between the distal end 18 and the proximal end 20. In some embodiments, a catheter 24 may be secured to the catheter adapter 16 and may extend distally from the catheter adapter 16. In some embodiments, the catheter 24 may include a PIVC, a midline catheter, or a peripherally inserted central catheter (PICC).

In some embodiments, the delivery device 12 may be coupled to any suitable catheter assembly. In these and other embodiments, the catheter assembly 14 may include a straight or non-integrated catheter assembly. In some embodiments, the catheter assembly 14 may include an integrated catheter assembly. In further detail, in some embodiments, the catheter adapter 16 of the catheter assembly 14 may include an integrated extension tube, such as, for example, the BD NEXIVA™ Closed IV Catheter System, the BD NEXIVA™ DIFFUSICS™ Closed IV Catheter System, or the Becton Dickinson PEGASUS™ Safety Closed IV Catheter System.

As illustrated in FIG. 1A, in some embodiments, the catheter adapter 16 may include a side port 26, which may be angled with respect to the distal end 18 of the catheter adapter 16. In some embodiments, the catheter assembly 14 may include an extension tube 28, which may include a distal end 30 and a proximal end 32. In some embodiments, the extension tube 28 may be short to provide near patient access. However, in some embodiments, a length of the extension tube 28 may vary. In some embodiments, the distal end 30 of the extension tube 28 may be coupled to the side port 26. In some embodiments, the distal end of the extension tube 28 may be integrated with the side port 26.

In some embodiments, a connector 34 may be coupled to the proximal end 32 of the extension tube 28. In some embodiments, the proximal end 32 of the extension tube 28 may be integrated with the connector 34. In some embodiments, the connector 34 may include a Y-adapter, a T-port, or another suitable connector. In some embodiments, the connector 34 may include a male or female luer connector with a luer-slip or luer-lock feature. In some embodiments, the connector 34 may include more than two ports.

In some embodiments, the connector 34 may include a first port 36 and a second port 38. In some embodiments, the delivery device 12 may be coupled to the first port 36 of the connector 34. In some embodiments, another extension tube 40 may be coupled to the second port 38 of the connector 34. In some embodiments, the catheter assembly 14 may include a needleless connector 39, and the delivery device 12 may be coupled to the first port 36 of the connector 34 via the needleless connector 39, which may be disposed between the delivery device 12 and the connector 34. In some embodiments, the connector 34 and the needleless connector 39 may be integrally formed. In some embodiments, the needleless connector 39 may include any suitable needleless connector.

In some embodiments, a proximal end 42 of the other extension tube 40 may include a connector 44, which may be coupled to any suitable blood collection device, such as a syringe, vacuum tube, blood collection tube, holder, etc. In some embodiments, the blood collection device may include or correspond to a fluid reservoir. In some embodiments, the connector 44 may include a male or female luer connector with a luer-slip or luer-lock feature. In some embodiments, the connector 44 may be coupled to a holder 46, which may be configured to receive another blood collection device. In some embodiments, the holder 46 may include a cannula configured to puncture a seal of a particular blood collection device. In some embodiments, the connector 44 may be coupled to a needleless connector 39, which may be coupled to the holder 46 or another blood collection device.

In some embodiments, the instrument, which may include a guidewire 48, may be delivered through the catheter assembly 14 via any suitable delivery device. In some embodiments, the delivery device 12 may include a housing 50, which may include a distal end 52, a proximal end 54, and a slot 56 which may extend between the distal end 52 and the proximal end 54. In some embodiments, the delivery device 12 may include the guidewire 48, which may include a proximal end 58 and a distal end 60.

In some embodiments, the delivery device 12 may include a guidewire hub 62, which may be disposed within the housing 50. In some embodiments, the guidewire 48 may be secured to the guidewire hub 62. In some embodiments, the guidewire hub 62 may be configured to move along the slot 56 to advance the guidewire 48 in a distal direction and distal to the distal end 52 of the housing 50. In some embodiments, the guidewire 48 may be advanced in the distal direction and/or retracted in a proximal direction. In some embodiments, the guidewire hub 62 and one or more other components of the delivery device 12 may be described further in U.S. Patent Application No. 62/660,646, filed Apr. 20, 2018, entitled "MULTI-DIAMETER CATHETER AND RELATED DEVICES AND METHODS," which is hereby incorporated by reference in its entirety.

In some embodiments, blood may flow proximally from the catheter 24 to the catheter adapter 16 to the extension tube 28 to the other extension tube 40. In some embodiments, blood may be prevented from entering the delivery device 12. For example, the distal end 52 of the housing 50 may include a septum 65 to prevent fluid, such as blood, from flowing into the distal end 52 of the housing 50. In other embodiments, blood may be permitted to flow proximally through the housing 50, and the housing 50 may include tubing coupled to a blood collection device. In some embodiments, the distal end 52 of the housing 50 may be coupled to a connector, which may include a male or female luer connector with a luer-slip or luer-lock feature, or another suitable connector. In some embodiments, the septum 65 may be disposed within the connector coupled to the distal end 52 of the housing 50, as illustrated, for example, in FIG. 1D.

Figure 1F:
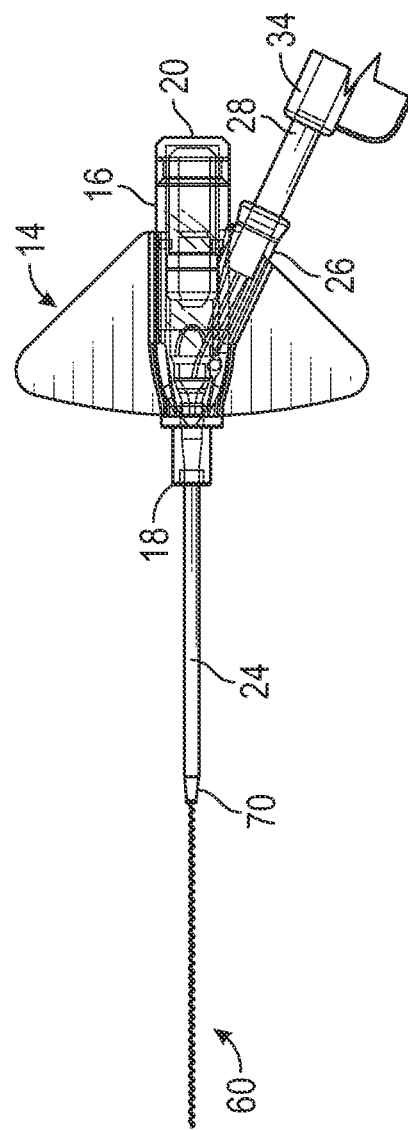
FIG. 1F is an enlarged upper perspective view of a portion of the catheter system of FIG. 1A, illustrating the guidewire in the advanced position, according to some embodiments.
Figure 1G:
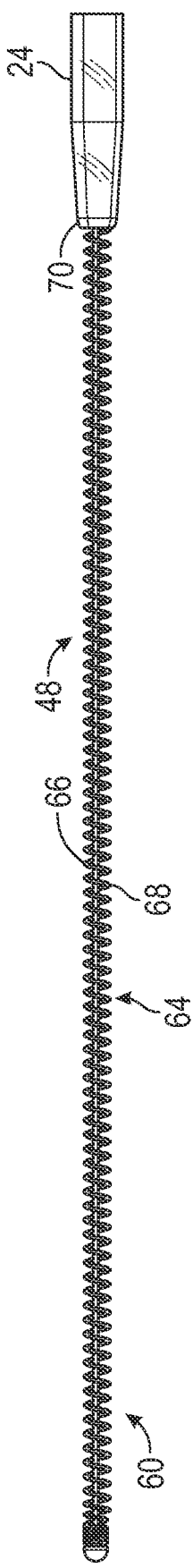
FIG. 1G is an upper perspective view of an example distal end of the catheter system of FIG. 1A, illustrating the guidewire in the advanced position, according to some embodiments.
Figure 1H:
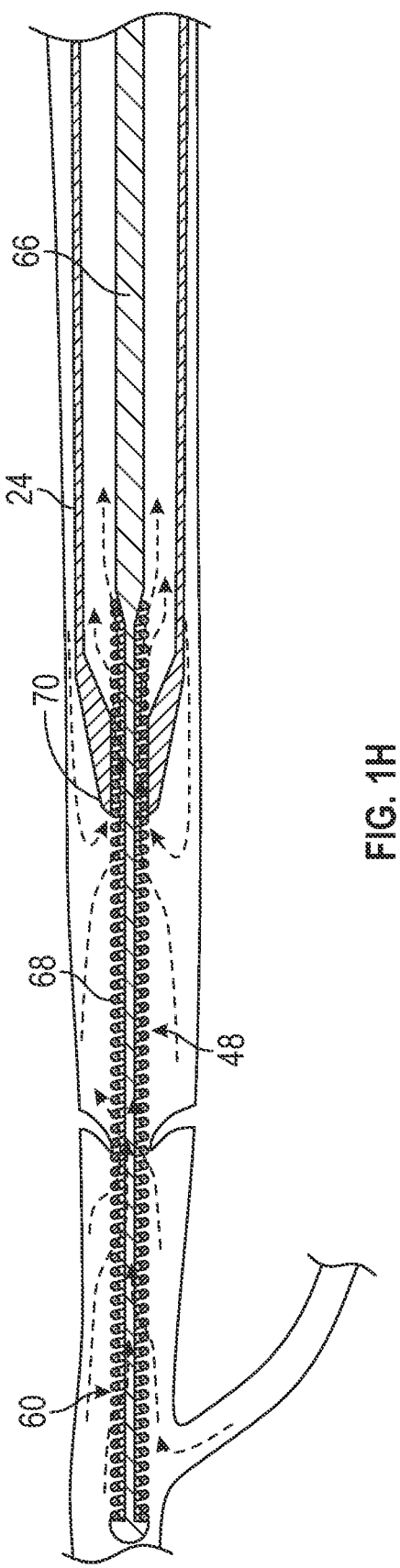
FIG. 1H is a cross-sectional view of an example distal end of the catheter system of FIG. 1A, illustrating the guidewire in the advanced position and disposed within vasculature of a patient, according to some embodiments.

Referring now to FIGS. 1F-1H, in some embodiments, the distal end 60 of the guidewire 48 may include a fluid permeable structure 64. In some embodiments, the fluid permeable structure 64 may include an elongated core 66 and a coil 68 extending around the elongated core 66. In some embodiments, blood may flow within a space between the elongated core 66 and the coil 68 in response to the guidewire 48 being inserted into vasculature of a patient.

In some embodiments, the guidewire 48 may be advanced beyond the distal tip 70 of the catheter 24, which may move or push away anything within the vasculature of the patient that might otherwise occlude the catheter 24 during a blood draw. For example, the guidewire 48 may move, push away, or move beyond fibrin material or thrombosis, or move the distal tip 70 of the catheter 24 away from a vein wall or a valve. As illustrated in FIG. 1H, in some embodiments, the guidewire 48 may push open a valve within the vasculature, allowing backflow of blood into the catheter 24. In some embodiments, the guidewire 48 may be left within the catheter 24 and extend beyond a distal tip 70 of the catheter during blood draw and/or fluid infusion.

In some embodiments, the fluid permeable structure 64 may include a long, narrow inlet path or multiple inlet paths into the distal tip 70 of the catheter 24. In some embodiments, the fluid permeable structure 64 may prevent fibrin material, thrombosis, or another material from obstructing the distal tip 70 of the catheter 24. In some embodiments, the delivery device 12 may include a gap between an outer diameter of the guidewire 48 and the catheter 24, which may allow blood to flow proximally through the gap from the vasculature. In some embodiments, the delivery device 12 may include a gap between the outer diameter of the guidewire 48 and the distal tip 70 of the catheter 24, which may allow blood to flow proximally through the gap from the vasculature.

In some embodiments, the catheter 24 and/or the catheter adapter 16 may be constructed from FEP, TEFLON, silicon, TPE, TPU, fluorinated polymers, or another suitable material. In some embodiments, the catheter 24 may be hydrophilic or hydrophobic. In some embodiments, the distal tip of the catheter 70 may be asymmetric. In some embodiments, the catheter 24 may include an anti-thrombogenic coating and/or an anti-fouling material.

Referring now to FIGS. 2A-2G, in some embodiments, the coil 68 may include a metal wire disposed in a helix about the elongated core 66. In some embodiments, the elongated core 66 may be solid and/or constructed of metal or other suitable material. In some embodiments, the elongated core 66 may be thin to provide some flexibility. In some embodiments, the elongated core 66 may be constructed of nitinol. In some embodiments, the coil 68 may be coupled to the elongated core 66.

In some embodiments, the guidewire 48 may include a rounded distal tip 72, which may reduce a risk of damage to the vasculature when the guidewire 48, which may be flexible, is inserted into the vasculature. In some embodiments, the rounded distal tip 72 may reduce a risk of thrombus development or other complications. In some embodiments, the rounded distal tip 72 may be spot welded or formed via another suitable means and/or materials.

In some embodiments, the coil 68 may include a distal end 74 and a proximal end 76. In some embodiments, the distal end 74 of the coil 68 may be coupled to the elongated core 66 via the rounded distal tip 72. In further detail, in some embodiments, the distal end of the coil 68 may be directly coupled to the rounded distal tip 72, which may be directly coupled to the elongated core 66.

In some embodiments, the coil 68 may be tightly wound around the elongated core 66 at one or more locations to couple the coil 68 to the elongated core 66. In some embodiments, the distal end 74 of the coil 68 may be tightly wound around the elongated core 66. In some embodiments, the proximal end 76 of the coil 68 may be tightly wound around the elongated core 66, as illustrated, for example, in FIG. 2A.

In some embodiments, the elongated core 66 may include a first portion 78, which may include a first outer diameter, and a second portion 80, which may include a second outer diameter. In some embodiments, the second outer diameter may be greater than the first outer diameter. In some embodiments, the coil 68 may be tightly wound around the second portion 80, as illustrated, for example, in FIG. 2F. In some embodiments, the elongated core 66 may be tapered or stepped between the first portion 78 and the second portion 80. In some embodiments, the guidewire 48 may include multiple diameters along its length, depending on, for example, corresponding inner diameters of the catheter assembly 14. In some embodiments, the elongated core 66 may include a uniform outer diameter, as illustrated, for example, in FIG. 2G, along an entirety of its length.

Figure 2A:
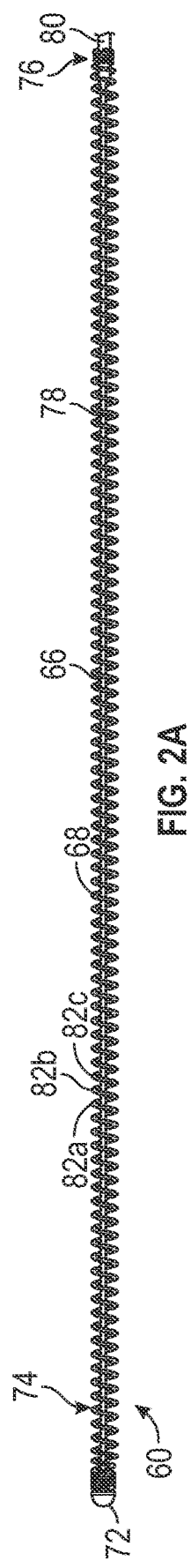
FIG. 2A is an upper perspective view of an example distal end of the guidewire of the catheter system of FIG. 1A, according to some embodiments.
Figure 2B:
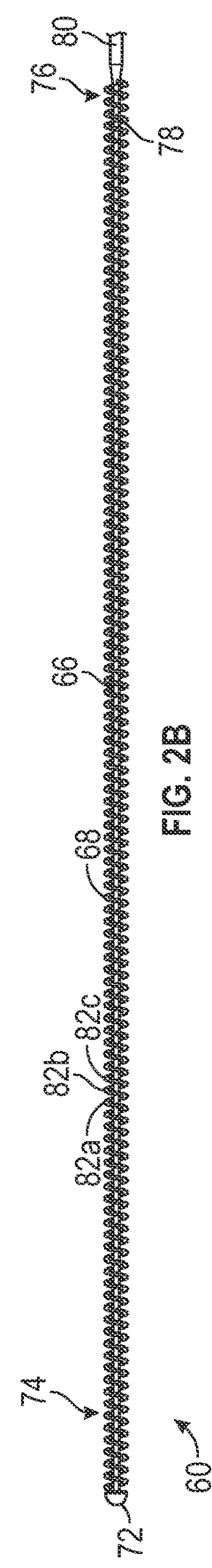
FIG. 2B is an upper perspective view of another example distal end of the guidewire of the catheter system of FIG. 1A, according to some embodiments.
Figure 2C:
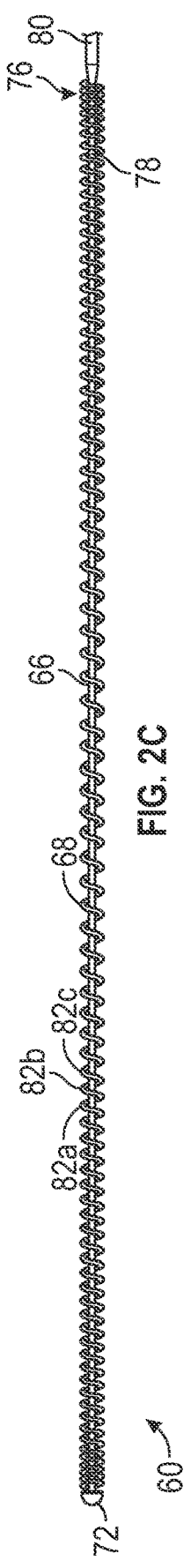
FIG. 2C is an upper perspective view of another example distal end of the guidewire of the catheter system of FIG. 1A, according to some embodiments.
Figure 2D:
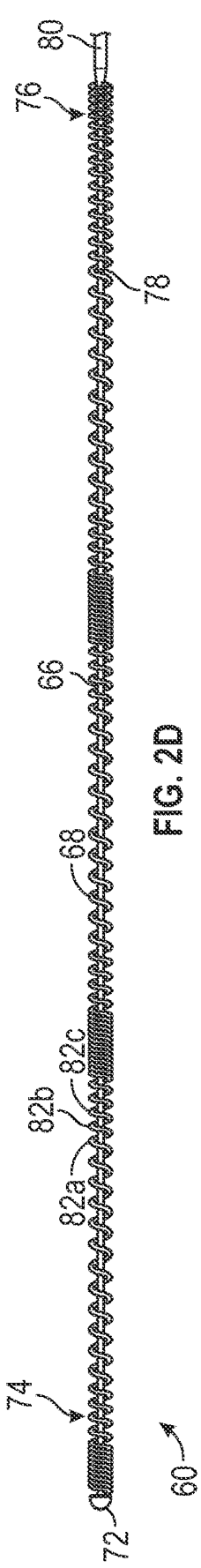
FIG. 2D is an upper perspective view of another example distal end of the guidewire of the catheter system of FIG. 1A, according to some embodiments.

In some embodiments, a spacing between rings 82 of the coil 68 may be generally uniform, as illustrated, for example, in FIGS. 2A-2B. In some embodiments, the spacing between rings 82 of the coil 68 may vary. As illustrated, for example, in FIG. 2D, in some embodiments, along one or more portions of the coil, the spacing of the rings 82 may be dense or tight (for example, the rings 82 may contact each other or be close to each other), while along other portions of the coil 68, the spacing of the rings may be more spread apart than along the portions of the coil 68.

Figure 2E:
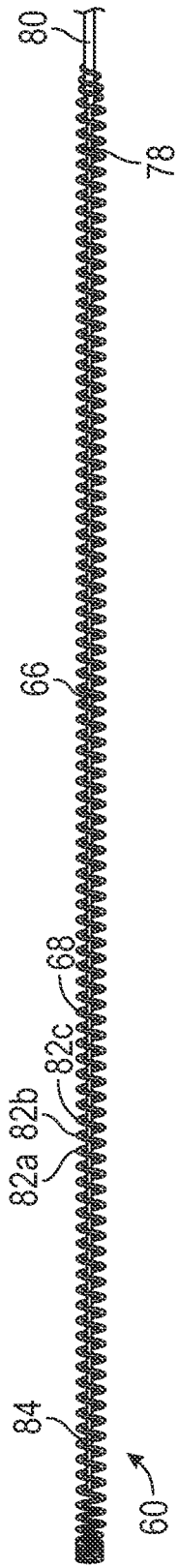
FIG. 2E is an upper perspective view of another example distal end of the guidewire of the catheter system of FIG. 1A, according to some embodiments.

As illustrated, for example, in FIG. 2E, in some embodiments, the distal end 74 of the coil 68 may be disposed distal to a distal end 84 of the elongated core 66. In these and other embodiments, the distal end 74 of the coil 68 may be open or closed. In some embodiments, the distal end 74 of the coil 68 may be closed by, for example, the rounded distal tip 72. In some embodiments, the distal end 74 of the coil 68 may be closed by spot welding, adhesive, over-molding, coupling with a plastic or elastomeric tip, or another suitable method. In some embodiments, the distal end 84 of the elongated core 66 may be blunt or rounded.

Figure 2F:
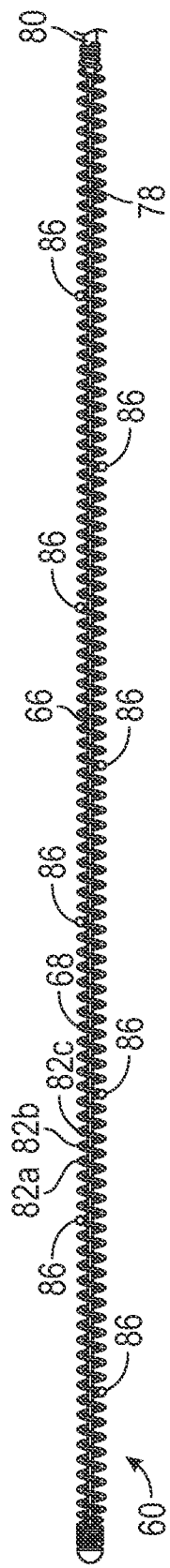
FIG. 2F is an upper perspective view of another example distal end of the guidewire of the catheter system of FIG. 1A, according to some embodiments.
Figure 2G:
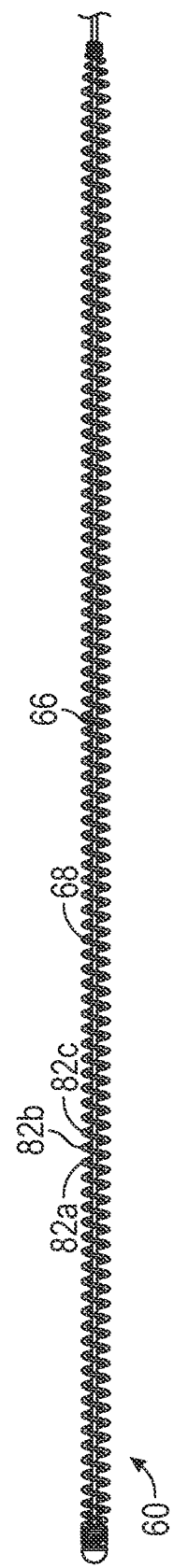
FIG. 2G is an upper perspective view of another example distal end of the guidewire of the catheter system of FIG. 1A, according to some embodiments.

As illustrated, for example, in FIG. 2F, in some embodiments, the coil 68 may be fixed to the elongated core 66 at one or more positions along a length of the elongated core 66. For example, one or more bridges 86 may extend from the coil 68 to the elongated core 66 to secure the coil 68 to the elongated core 66 at one or more points along a length of the coil 68. In these and other embodiments, the elongated core 66 may extend along a central axis of the coil 68. In some embodiments, the delivery device 12 may include any suitable elongated core and/or any suitable coil. In some embodiments, the bridges 86 may be formed by welding, adhesive, or another suitable means.

In some embodiments, the elongated core 66 may not extend along the central axis of the coil 68. In these embodiments, the elongated core 66 may be offset from the central axis of the coil 68. In these and other embodiments, the elongated core 66 may contact the coil 68 at multiple contact points along the length of the coil 68 and/or may be coupled to the coil 68 at one or more of the contact points. In some embodiments, the elongated core 66 may be coupled to the coil 68 by welding, adhesive, or another suitable means.

Figure 3A:
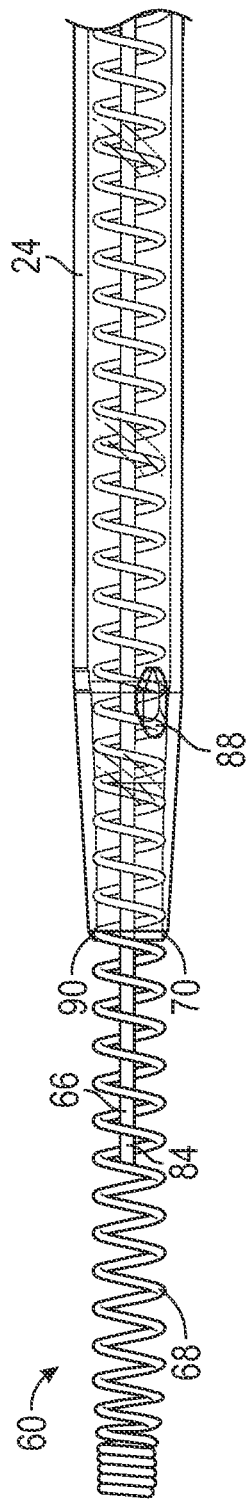
FIG. 3A is an upper perspective view of another example distal end of the catheter system of FIG. 1A, illustrating the guidewire in the advanced position and an example diffuser hole, according to some embodiments.
Figure 3B:
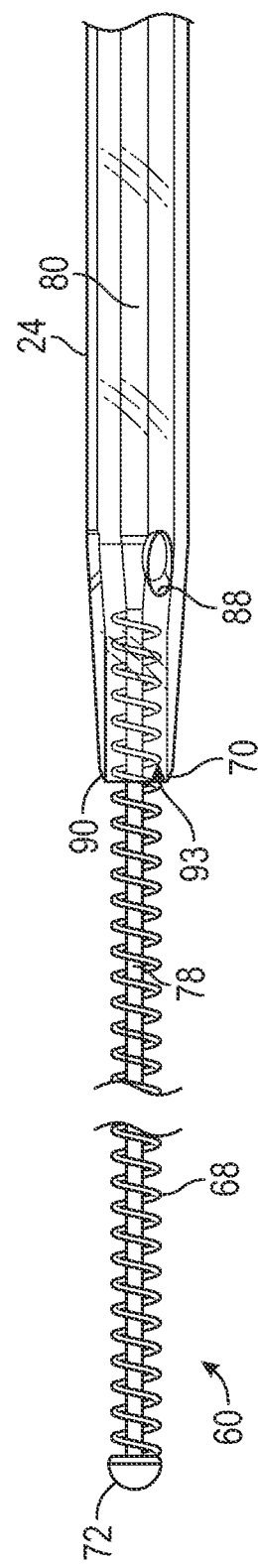
FIG. 3B is an upper perspective view of another example distal end of the catheter system of FIG. 1A, illustrating the guidewire in the advanced position and the diffuser hole, according to some embodiments.

Referring now to FIGS. 3A-3B, in some embodiments, the catheter 24 may include one or more diffuser holes 88, which may provide additional paths for blood to enter the catheter 24. In some embodiments, the coil 68 may extend into the catheter 24. In some embodiments, the coil 68 may extend through all or a portion of the catheter 24. In some embodiments, the coil 68 may extend proximally beyond the diffuser holes 88. In some embodiments, some embodiments, the coil 68 may not extend proximally beyond the diffuser holes 88.

In some embodiments, the second portion 80 may be disposed proximal to a distal opening 90 of the catheter 24. In some embodiments, the delivery device 12 may include the gap 93 between an outer diameter of the guidewire 48 and the distal opening 90 of the catheter 24, which may allow blood to flow proximally through the gap 93 from the vasculature. In some embodiments, the elongated core 66 may be sized according to a specific catheter gauge size it may be used with.

In some embodiments, an outer diameter of the coil 68 and/or the elongated core 66 may be variable, tapered, or straight. In some embodiments, the outer diameter of the coil 68 may be greater than a diameter of the distal opening 90 of the catheter 24 and the coil 68 may be compressible.

Figure 4A:
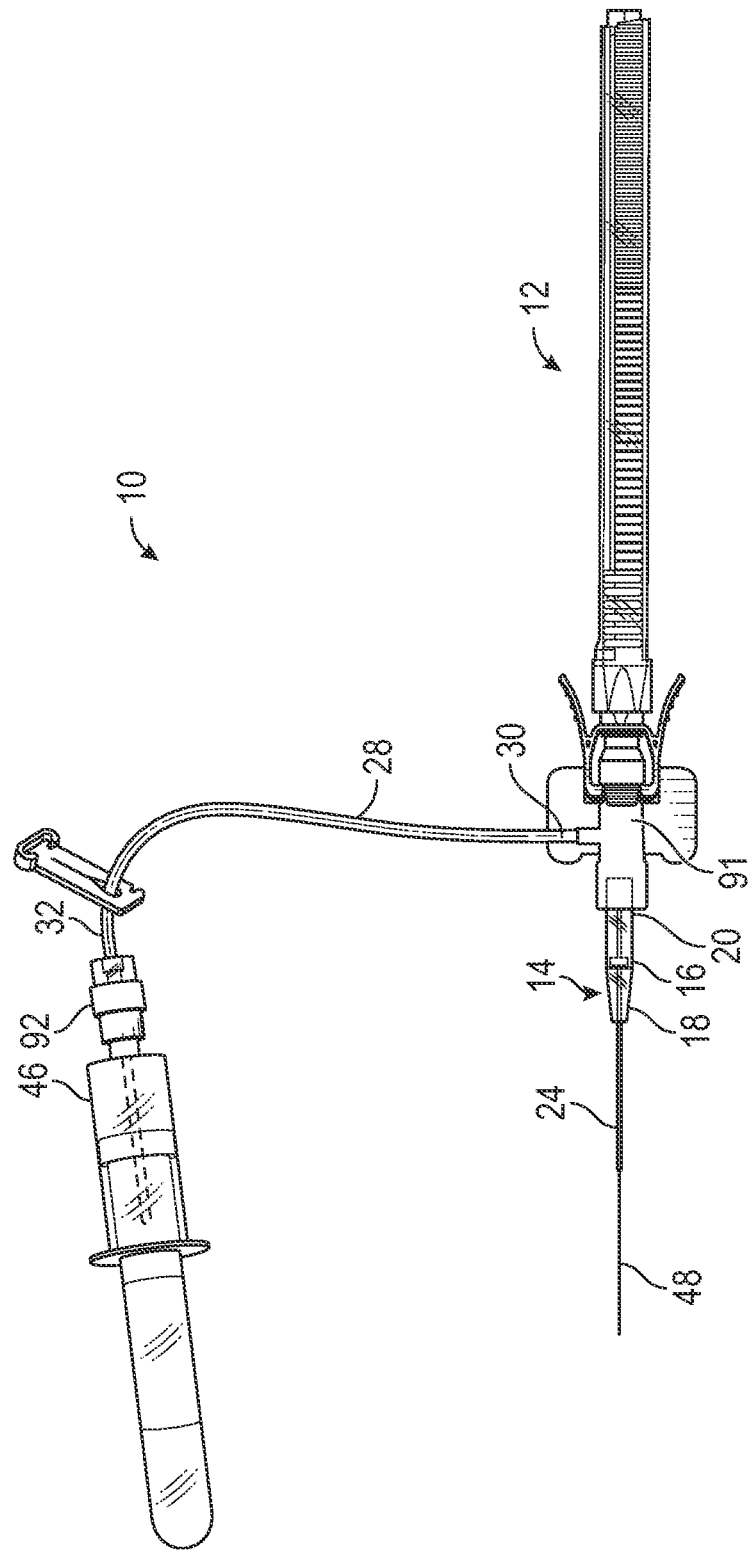
FIG. 4A is an upper perspective view of another example catheter assembly of the catheter system of FIG. 1A, according to some embodiments.

Referring now to FIG. 4A, in some embodiments, the delivery device 12 may be coupled to a proximal port of a T-connector 91, which may include a needleless connector. In some embodiments, a distal port of the T-connector 91 may be coupled to the proximal end 20 of the catheter adapter 16. In these and other embodiments, the catheter adapter 16 may not include the side port 26 and/or an integrated extension tube. In some embodiments, the extension tube 28 may be coupled to a side port of the T-connector, which may be angled with respect to the proximal port and the distal port.

In some embodiments, the fluid pathway of the catheter system 10 may include the catheter 24, the catheter adapter 16, the T-connector, and the extension tube 28. In some embodiments, the proximal end 32 of the extension tube 28 may be coupled to a connector 92, which may be coupled to any suitable blood collection device. In some embodiments, the connector 92 may include a male or female luer connector with a luer-slip or luer-lock feature. In some embodiments, the connector 92 may be coupled to a needleless connector 39, which may be coupled to the holder 46 or another blood collection device.

In some embodiments, the connector 92 may be coupled to the holder 46, which may be configured to receive a particular blood collection device, such as a blood collection tube, vacuum tube, or a syringe. In some embodiments, the holder 46 may include a cannula configured to puncture a seal of the particular blood collection device.

Figure 4B:
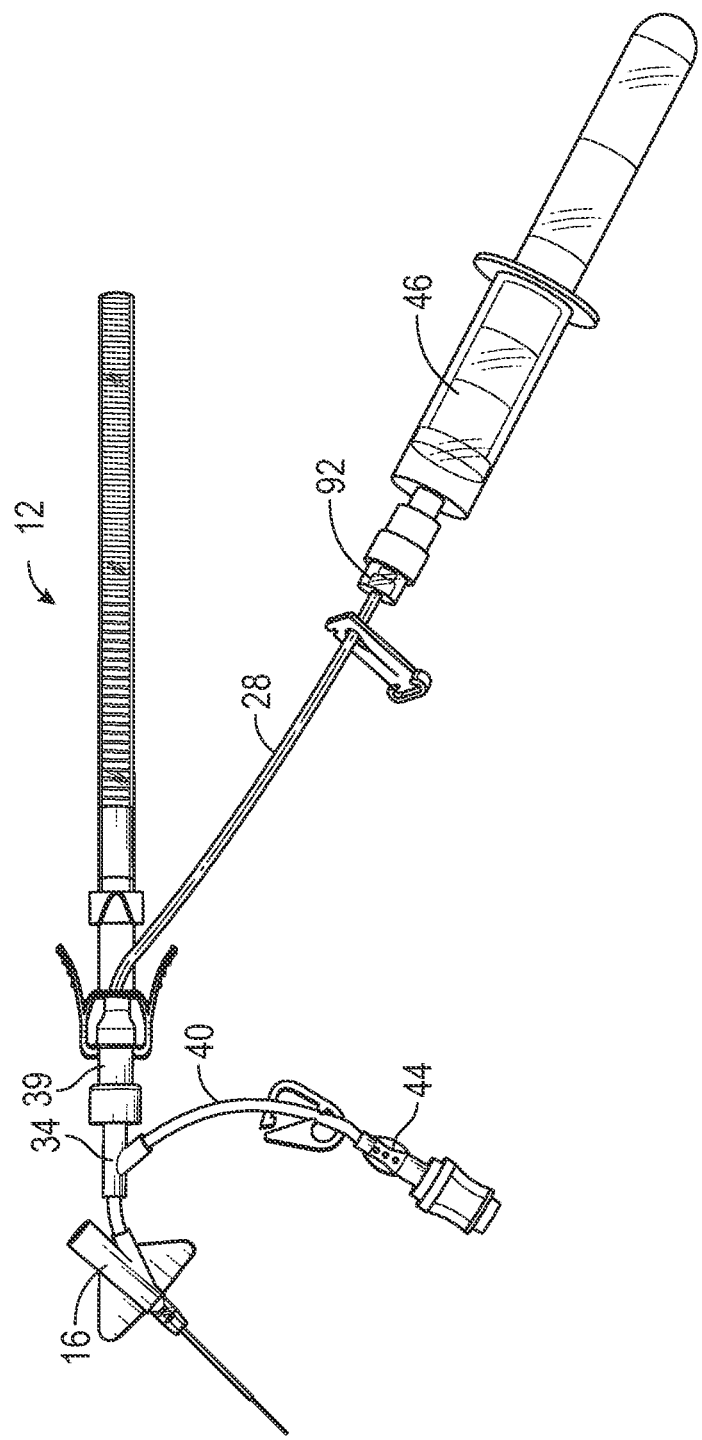
FIG. 4B is an upper perspective view of the delivery device of the catheter system of FIG. 1A, according to some embodiments.

Referring now to FIG. 4B, in some embodiments, the extension tube 40 may extend from the delivery device 12. For example, the connector coupled to the distal end 52 of the housing 50 may include a port or the housing 50 may include a port. In some embodiments, the extension tube 40 may be coupled to and/or integrated with the port. In some embodiments, the delivery device 12 may include a septum at the distal end of the housing 20 or within the connector. In some embodiments, the septum may be proximal to the port, which may prevent blood from moving proximal to the septum and from travelling through a majority of the housing 50.

Figure 5A:
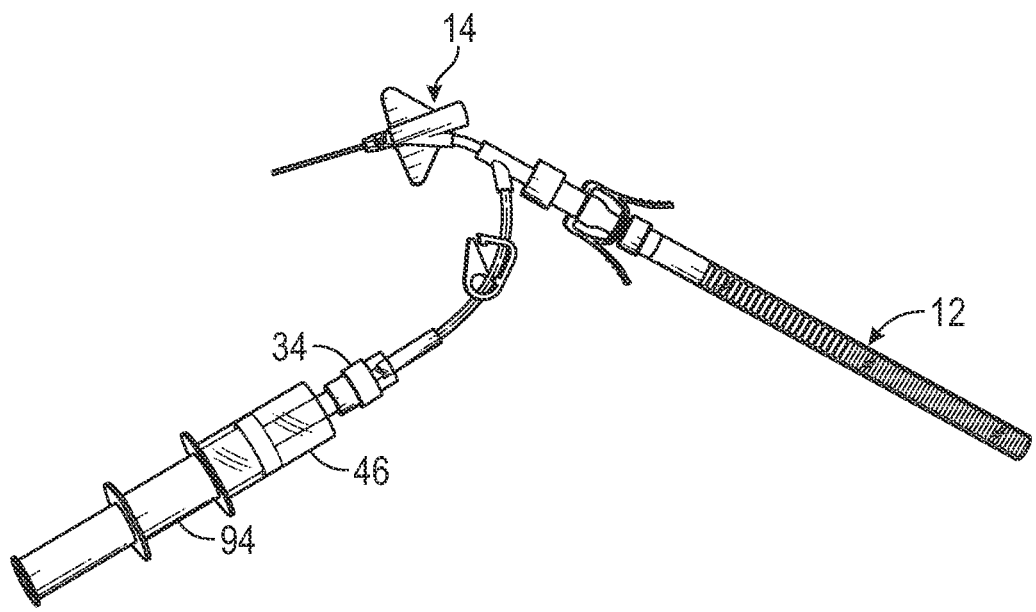
FIG. 5A is an upper perspective view of the catheter system of FIG. 1A, illustrating an example syringe, according to some embodiments.
Figure 5B:
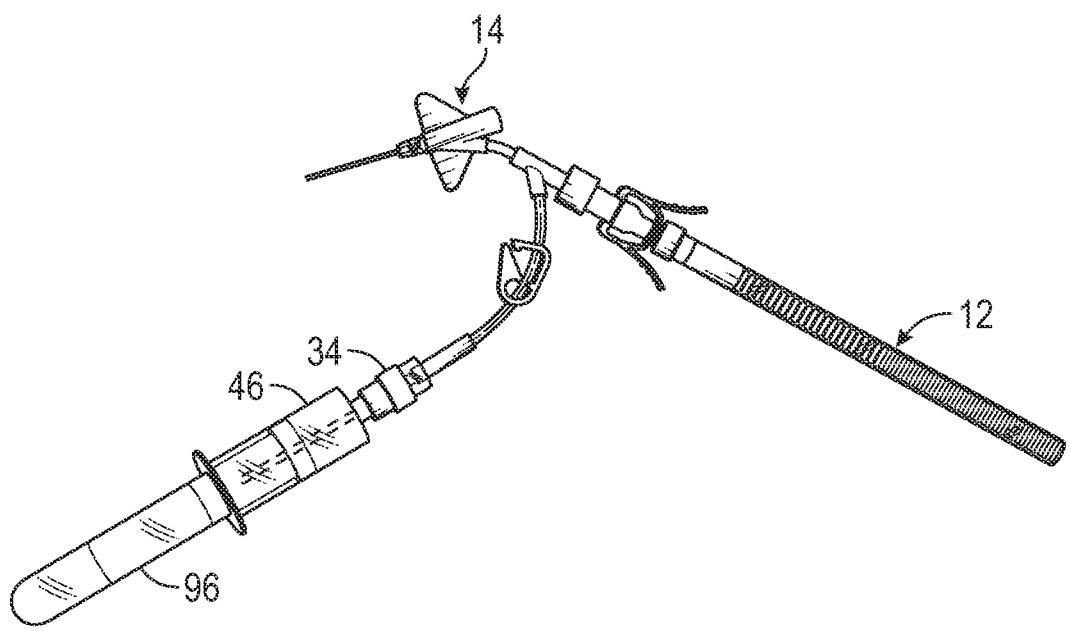
FIG. 5B is an upper perspective view of the catheter system of FIG. 1A, illustrating the syringe replaced with a blood collection tube, according to some embodiments.

Referring now to FIG. 5A, the holder 46 is illustrated coupled to an example flush syringe 94, which may be pre-filled with saline. Referring now to FIG. 5B, the holder 46 is illustrated coupled to an example blood collection tube 96. In some embodiments, after the flush syringe 94 is used to flush the catheter 24 to ensure patency and to pull an initial discard sample into the flush syringe 94, the flush syringe 94 may be uncoupled from the connector 34 (or the connector 92 discussed with respect to FIG. 4) and the blood collection tube 96 or another suitable blood collection device may be coupled to the connector 92.

Figure 6C:
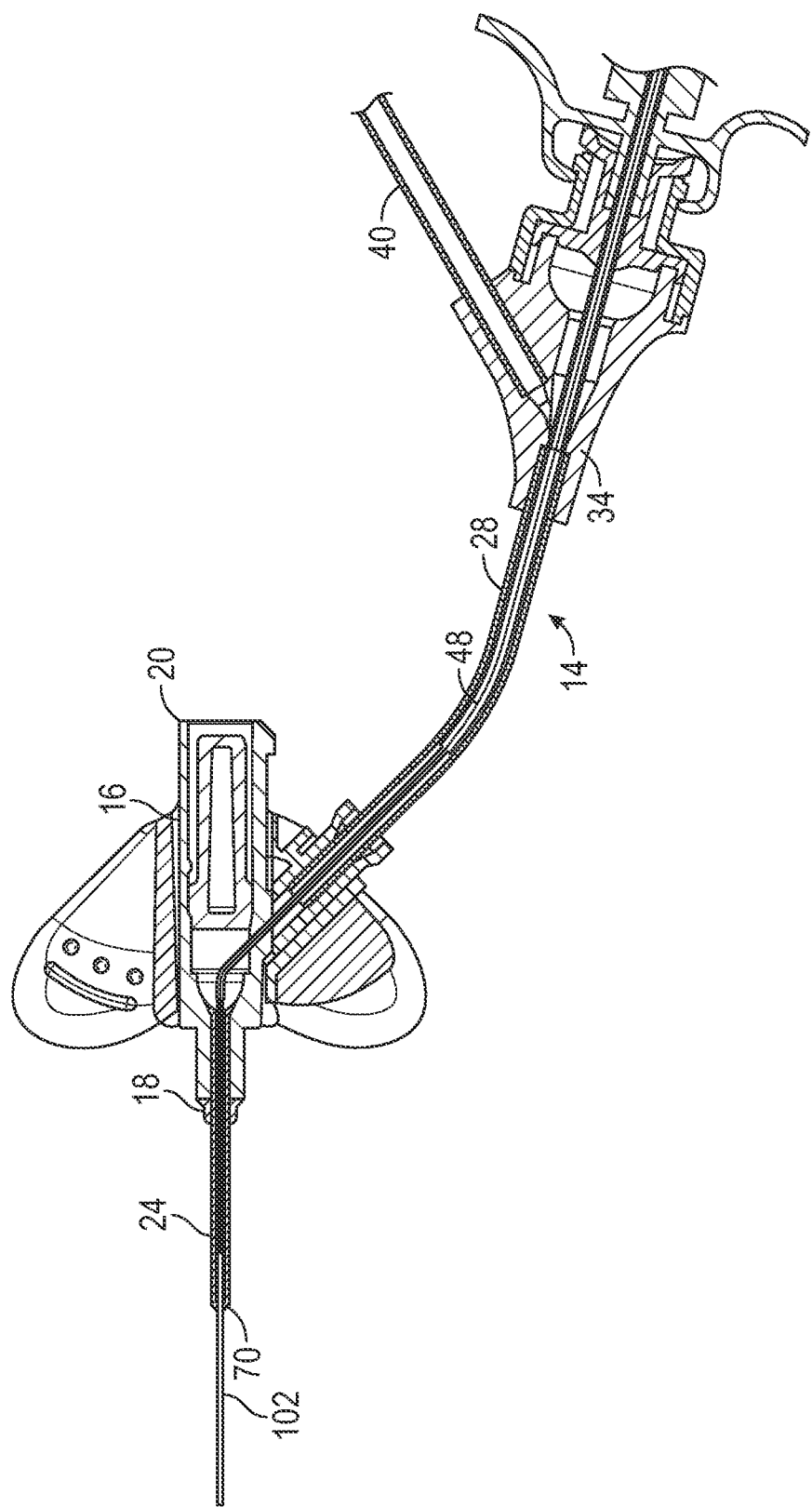
FIG. 6C is a cross-sectional view of the other delivery device of FIG. 6A coupled to another example catheter assembly, illustrating the guidewire partially advanced, according to some embodiments.

Referring now to FIGS. 6A-6C, in some embodiments, a delivery device 100 is illustrated, according to some embodiments. In some embodiments, the delivery device 100 may be similar, or identical, in terms of one or more included components and/or operation as the delivery device 12 disclosed in FIGS. 1-5 in the present disclosure. In some embodiments, the delivery device 100 may include tubing 102, which may include a proximal end 104 and a distal end 106.

In some embodiments, the tubing 102 may be configured to extend into and/or through the catheter 24 into the vasculature of a patient. In some embodiments, the guidewire 48 may be disposed within the tubing 102 and/or may extend distally through the tubing 102 when the guidewire 48 is advanced. In some embodiments, the guidewire 48 may be fully retracted when the tubing 102 is advanced, as illustrated, for example, in FIGS. 6A-6B. In some embodiments, the guidewire 48 and the tubing 102 may be advanced and/or retracted simultaneously.

In some embodiments, the guidewire and/or the tubing 102 may reduce a number of needle sticks that a patient experiences as the catheter may be replaced less frequently. In some embodiments, the tubing 102 may allow a user to draw a blood sample or infuse fluid through the catheter 24 when the catheter 24 is no longer functional or less effective due to, for example, debris build up on the distal end of the catheter 24 or collapse of the catheter 24.

In some embodiments, the delivery device 100 may include a tubing hub 107 disposed within the housing 50. In some embodiments, the tubing 102 may be secured to the tubing hub 107. In some embodiments, the tubing hub 107 may be configured to move along the slot 56 to advance the tubing 102 in a distal direction distal to the distal end 52 of the housing 50. In some embodiments, the tubing 102 may be advanced in the distal direction and/or retracted in the proximal direction. In some embodiments, the tubing 102, the guidewire hub 62, the tubing hub 107, and one or more other components of the delivery device 100 may be described further in U.S. Patent Application No. 62/660,646, filed Apr. 20, 2018, entitled "MULTI-DIAMETER CATHETER AND RELATED DEVICES AND METHODS," which is hereby incorporated by reference in its entirety.

Referring now to FIGS. 7A-7D, in some embodiments, a delivery device 108 is illustrated, according to some embodiments. In some embodiments, the delivery device 108 may be similar, or identical, in terms of one or more included components and/or operation as the delivery device 12 disclosed in FIGS. 1-5 and/or the delivery device 100 disclosed in FIG. 6 in the present disclosure.

In some embodiments, the delivery device 108 may include tubing 110, which may include a proximal end 112 and a distal end 114. In some embodiments, the proximal end 112 of the tubing 110 may be coupled to a connector 116, which may include a male or female luer connector with a luer-slip or luer-lock feature. In some embodiments, the connector 116 may be coupled to any suitable blood collection device. In some embodiments, the connector 116 may be coupled to the holder 46, which may be configured to receive another blood collection device. In some embodiments, the proximal end 58 of the guidewire 48 and/or the distal end 114 of the tubing 110 may be secured within a hub 115.

In some embodiments, a proximal end of the tubing 102 may be secured within the hub 115. In some embodiments, guidewire 48 may be longer than the tubing 102 and may extend distally beyond the distal end 52 of the housing 50.

Figure 7A:
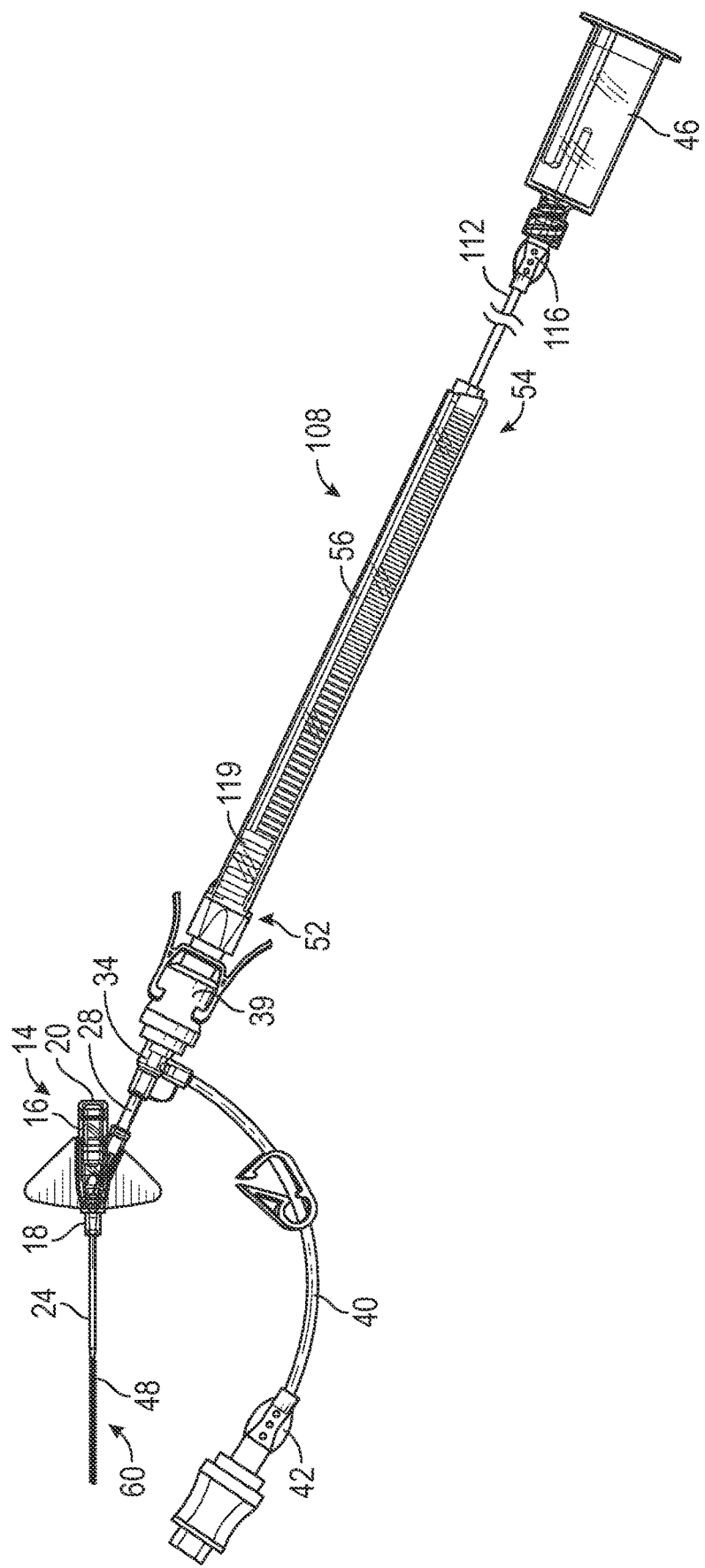
FIG. 7A is an upper perspective view of another delivery device, coupled with the catheter system of FIG. 1A, according to some embodiments.
Figure 7B:
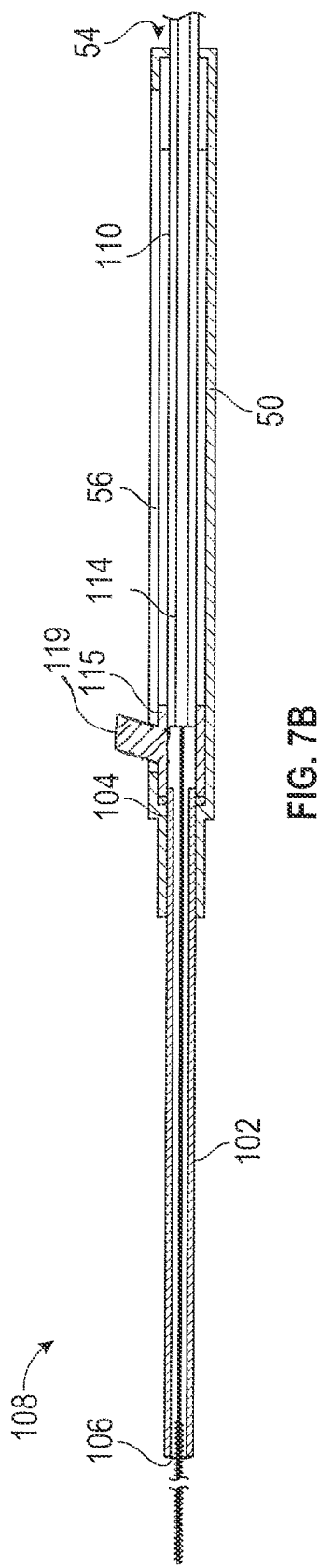
FIG. 7B is a cross-sectional view of the delivery device of FIG. 7A, illustrating the guidewire and example tubing in an advanced position, according to some embodiments.
Figure 7C:
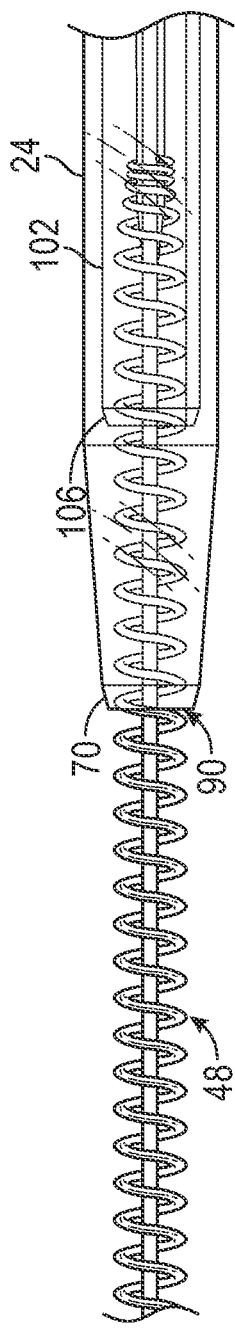
FIG. 7C is an upper perspective view of the delivery device of FIG. 7A coupled to the catheter system of FIG. 1A, according to some embodiments.
Figure 7D:
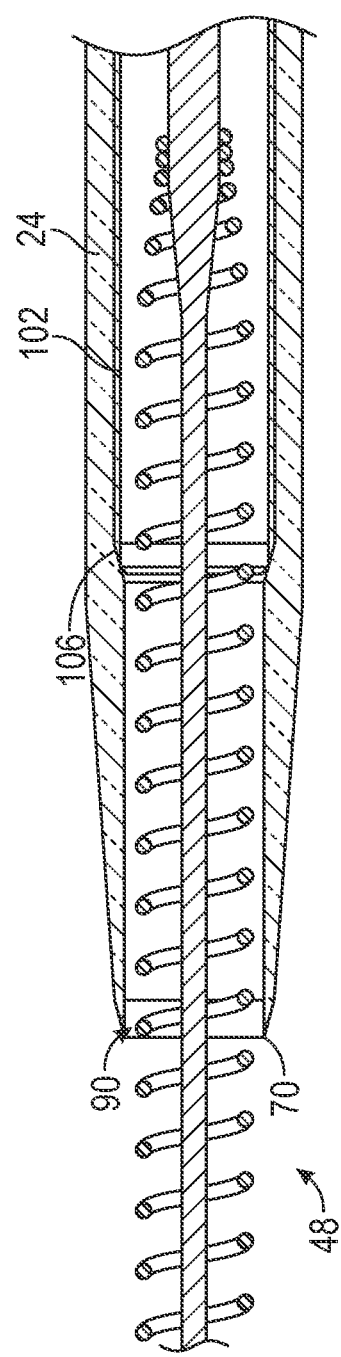
FIG. 7D is a cross-sectional view of the delivery device of FIG. 7A coupled to the catheter system of FIG. 1A, according to some embodiments.

In some embodiments, the hub 115 may include an advancement tab 119 within the slot 56. In some embodiments, the hub 115 may be moved distally within the slot 56 to simultaneously advance the guidewire 48 and the tubing 102 in the distal direction. FIGS. 7B-7D illustrate the guidewire 48 and the tubing 102 fully advanced in the distal direction, according to some embodiments. In some embodiments, the hub 115 may be moved proximally to retract the guidewire 48 and the tubing 102. In some embodiments, in response to the tubing 102 being fully advanced in the distal direction, the distal end 106 of the tubing 102 may be disposed or terminate proximal to distal tip 70 of the catheter 24, which may allow the tubing 102 to include a larger outer diameter and/or improved visualization of the distal end 114 in the fully advanced position.

In some embodiments, in response to the tubing 102 being fully advanced in the distal direction, the distal end 106 of the tubing 102 may be disposed or terminate distal to the distal tip 70 of the catheter 24, even with the distal tip 70, proximal to the distal tip 70, proximate a catheter wedge, or proximal to the catheter wedge within the catheter adapter 16. In some embodiments, an outer diameter of the distal end 106 may provide a seal wherever it terminates, which may reduce mixing of blood drawn with fluids in the catheter assembly 14, reducing a waste volume. In some embodiments, in response to the tubing 102 being fully advanced in the distal direction, the distal end 106 of the tubing 102 may be disposed anywhere within the fluid pathway. In some embodiments, the coil 68 may be disposed within the tubing 102.

Figure 7E:
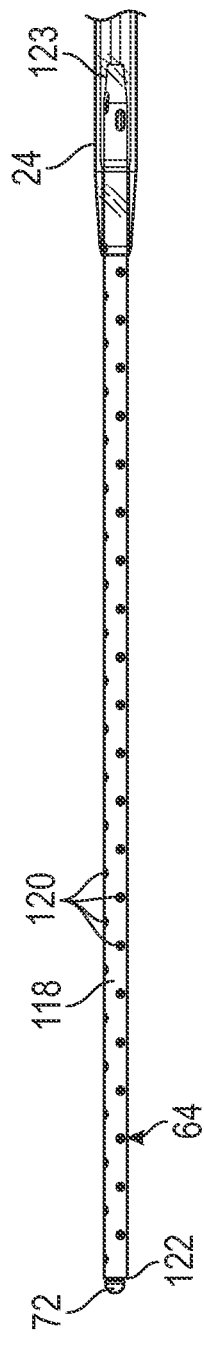
FIG. 7E is an upper perspective view of another example distal end of the catheter system of FIG. 1A, according to some embodiments.
Figure 7F:
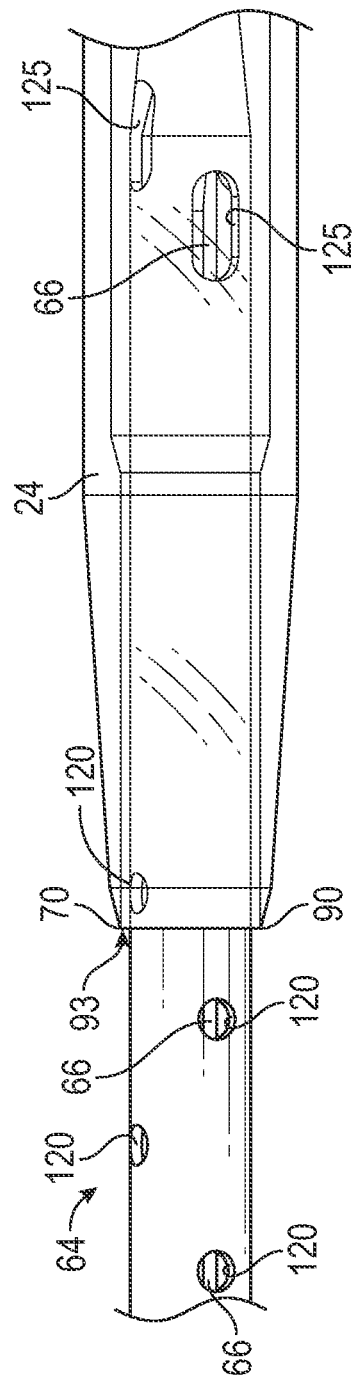
FIG. 7F is an enlarged upper perspective view of the other distal end of FIG. 7E, according to some embodiments.

Referring now to FIGS. 7E-7H, in some embodiments, the guidewire 48 may include a tube 118 in addition to or as an alternative to the coil 68. In some embodiments, the tube 118 may include the fluid permeable structure 64. For example, in some embodiments, the tube 118 may be porous. As illustrated in FIG. 7E, in some embodiments, the tube 118 may include multiple holes 120, which may be arranged in various patterns and numbers and may include various sizes. In some embodiments, the holes 120 may be disposed on a distal end 122 of the tube 118. In some embodiments, the holes 120 may be arranged in staggered rows.

In some embodiments, the distal end 122 of the tube 118 may be open or closed. In some embodiments, the distal end 122 of the tube 118 may be coupled to the rounded distal tip 72. In some embodiments, a proximal end 123 of the tube 118 may be disposed within the catheter 24 and/or tapered. In some embodiments, the proximal end 123 of the tube 118 may include one or more holes 125, which may be larger and/or fewer than the holes 120. In some embodiments, the proximal end 123 of the tube 118 may be coupled to the elongated core 66.

Figure 7G:
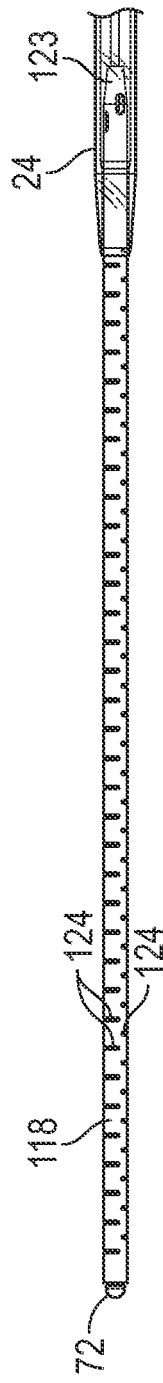
FIG. 7G is an upper perspective view of another example distal end of the catheter system of FIG. 1A, according to some embodiments.
Figure 7H:
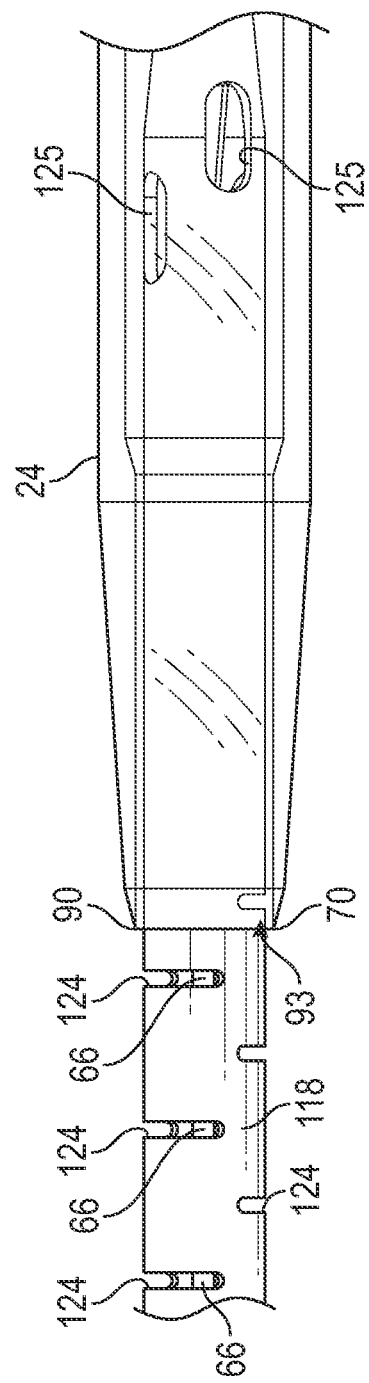
FIG. 7H is an enlarged upper perspective view of the other distal end of FIG. 7G, according to some embodiments.
Figure 8I:
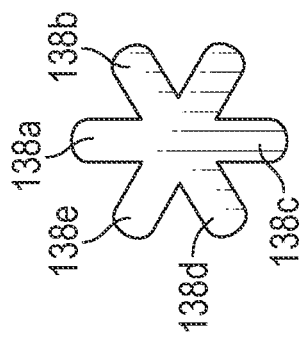
FIG. 8I is a cross-sectional view of the other distal end along the line 8I-8I of FIG. 8H, according to some embodiments.
Figure 8J:
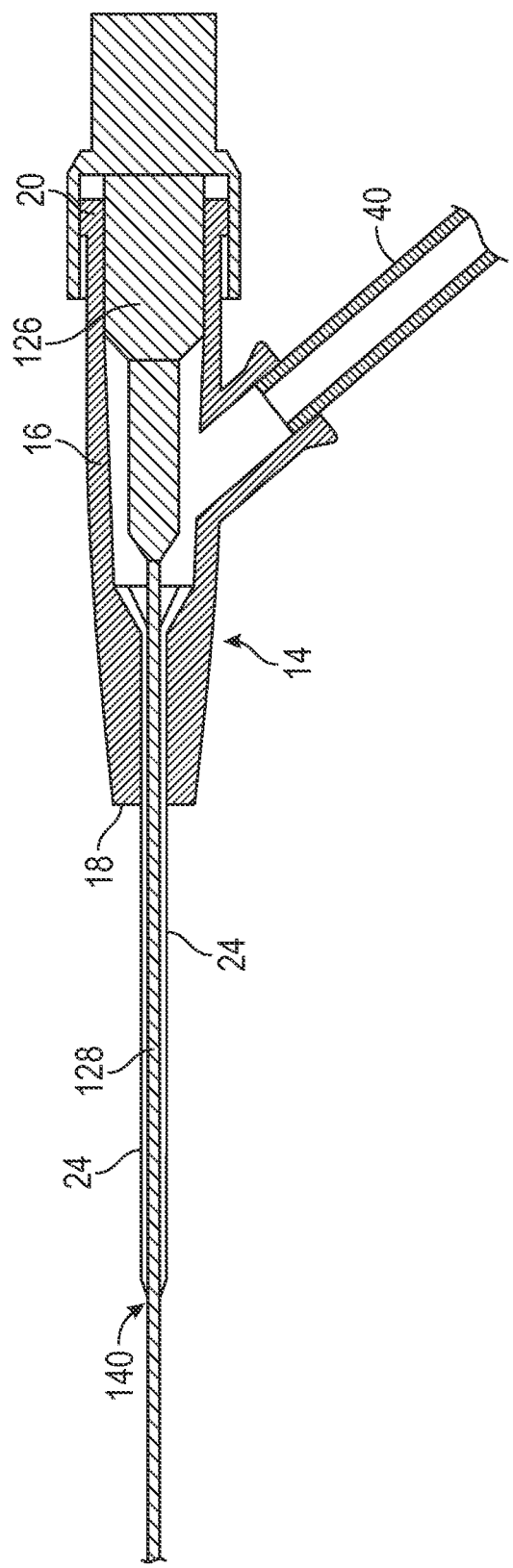
FIG. 8J is a cross-sectional view of an example catheter assembly, illustrating another example extension device, according to some embodiments.

As illustrated in FIG. 7G, in some embodiments, the tube 118 may include multiple slits 124, which may be arranged in various patterns and numbers and may include various sizes. In some embodiments, the slits 124 may be disposed on the distal end 122 of the tube 118. In some embodiments, the slits 124 may be arranged in staggered rows. In some embodiments, the slits 124 may be cut generally perpendicular to a longitudinal axis of the catheter 24, although in some embodiments, angles of the slits 124 may vary. In some embodiments, the elongated core 66 may extend partially or completely through the tube 118.

Referring now to FIG. 8A-8J, the catheter system 10 may include an extension device 126, which may include an elongated body 128. In some embodiments, the elongated body 128 may include a fluid permeable structure 130 that may be configured to allow fluid to enter the distal end 18 of the catheter 24 in response to the extension device 126 being inserted through the catheter 24.

In some embodiments, the fluid permeable structure 130 of the extension device 126 may include a groove, as illustrated, for example in FIGS. 8A-8D. In some embodiments, the fluid permeable structure 130 of the extension device 126 may include a flat region, as illustrated, for example, in FIGS. 8E-8F. In some embodiments, the flat region may include a generally planar upper surface 132 opposite a generally planar lower surface 134. In some embodiments, the flat region may provide two inlets into the catheter 24. In some embodiments, the fluid permeable structure 130 of the extension device 126 may include multiple side holes 136, which may be connected by a lumen of the elongated body 128.

In some embodiments, the extension device 126 may be solid. In some embodiments, the elongated body 128 may include a shape with multiple arms 138 extending away from each other and angled with respect to each other, as illustrated, for example, in FIGS. 8H-8I. In some embodiments, a shape of the elongated body 128 may vary. In some embodiments, a gap 140 may be disposed between an outer diameter of the extension device 126 and the distal opening 90 of the catheter 24, which may allow blood to flow proximally through gap 140 from the vasculature. In some embodiments, a blood collection device may be coupled to the proximal end of the extension tube 40.

Referring now to FIGS. 9-10, a delivery device 146 may include a hub 115 disposed within the housing 50, which may include a guide feature. In some embodiments, the delivery device 146 may be similar, or identical, in terms of one or more included components and/or operation as the delivery device 12 disclosed in FIGS. 1-5, the delivery device 100 disclosed in FIG. 6, the delivery device 108 disclosed in FIG. 7.

In some embodiments, the hub 115 may extend through the slot 56. In some embodiments, the guide feature may include a channel, which may be generally U-shaped. In some embodiments, the guide feature, the hub 115, the channel, and other features of the delivery device 146 may be further illustrated, for example, in U.S. Patent Application No. 62/696,229, filed Jul. 10, 2018, entitled "DELIVERY DEVICE FOR A VASCULAR ACCESS INSTRUMENT," which is hereby incorporated by reference in its entirety. In some embodiments, the guide feature may include an advancement tab 119, which may be configured to be moved by a hand of a user.

In some embodiments, the delivery device 146 may include the guidewire 48 disposed within the housing 50 and extending through the guide feature. For example, in some embodiments, the guidewire 48 may extend through the channel. In some embodiments, in response to movement of the guide feature along the slot 56 in the distal direction a first distance, the distal end 60 of the guidewire 48 may be advanced in the distal direction a second distance, which may be greater than the first distance. In some embodiments, the second distance may be two times the first distance.

In some embodiments, the proximal end 58 of the guidewire 48 may be stationary with respect to the housing 50. In some embodiments, the proximal end 58 may be fixed within the housing 50. In some embodiments, the distal end 60 may be advanced in the distal direction beyond the distal end of the housing 50 in response to the guide feature being partially and/or fully advanced along the slot 56 in the distal direction. In these and other embodiments, the housing 50 may include extension tubing 40, which may extend outwardly from a distal portion of the housing 50, and may be coupled to a blood collection device.

As illustrated in FIGS. 10A-10B, in some embodiments, the delivery device 146 may include the tubing 102, which may extend from and be coupled to the hub 115. In some embodiments, in response to movement of the guide feature along the slot 56 in the distal direction, the guidewire 48 may move through the tubing 102. In some embodiments, in response to movement of the guide feature along the slot 56 in the distal direction the first distance, the distal end 106 of the tubing 102 may be advanced in the distal direction a distance equal to the first distance (a "1:1 advancement ratio"), while the distal end 60 of the guidewire 48 may be advanced a distance greater than that of the first distance, such as for example, twice the first distance ("a 1:2 advancement ratio"). In some embodiments, when the guidewire 48 and the tubing 102 are fully advanced, the distal end 60 of the guidewire 48 may be distal to the distal tip 70 of the catheter 24. In these and other embodiments, the distal end 60 of the tubing 102 may be disposed distal to the distal tip 70 of the catheter 24, even with the distal tip 70 of the catheter 24, or proximal to the distal tip 70 of the catheter 24.

Figure 10C:
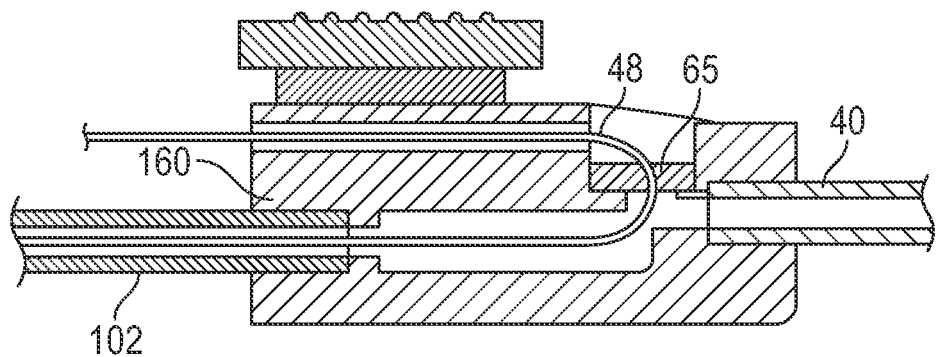
FIG. 10C is a cross-sectional view of an example hub of the delivery device of FIG. 10A, according to some embodiments.

In some embodiments, a septum 65 may be disposed at various locations within a distal end of the delivery device 146. As illustrated, for example, in FIG. 9A-9B, the septum 65 may be disposed proximal to the coupling point of the extension tubing 40 and/or distal to a distal end of the slot 56. As illustrated, for example, in FIGS. 10A-10B, the septum 65 may be disposed at the distal end of the housing 50 or within the connector coupled to the distal end of the housing 50. In some embodiments, the septum 65 may be disposed within the hub 115, as illustrated, for example, in FIG. 10C. As illustrated in FIG. 10C, in some embodiments, the extension tube 40 may extend proximally from the hub 115 and/or through the proximal end of the housing 50.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention. It should be understood that any of the delivery devices and/or one or more included components may be combined with one or more components of one or more of the catheter assemblies described in the present disclosure. It should be understood that one or more components of a particular delivery device may be combined with one or more components of another particular delivery device. For example, any fluid permeable structure described with respect to a particular delivery device may be combined with one or more components of another particular delivery device.

What is claimed is:

1. A delivery device to deliver an instrument through an intravenous catheter assembly, the delivery device comprising:
   a housing having a distal end and a proximal end, wherein the distal end of the housing comprises a connector; and
   a fluid-permeable instrument comprising:
      an elongated core having a proximal end and a distal end; and
      a tube having a proximal end and a distal end, the tube at least partially surrounding the elongated core,
   wherein the instrument is configured to advance distally from the housing,
   wherein the distal end of the tube is configured to extend beyond a distal end of a catheter of the intravenous catheter assembly.

2. The delivery device of claim 1, wherein the housing comprises a slot, wherein the delivery device further comprises:

a hub disposed within the housing, wherein the elongated core is secured to the hub, wherein the hub is configured to move along the slot to advance the instrument in a distal direction and distal to the distal end of the housing.

3. The delivery device of claim 1, wherein the instrument further comprises a coil extending around the elongated core and coupled to the elongated core, the coil received between the tube and the elongated core.

4. The delivery device of claim 3, wherein the coil is fixed to the elongated core at a plurality of positions along a length of the elongated core.

5. The delivery device of claim 3, wherein spacing between rings of the coil is generally uniform.

6. The delivery device of claim 3, wherein spacing between rings of the coil varies.

7. The delivery device of claim 1, wherein the instrument comprises a rounded distal tip.

8. The delivery device of claim 7, wherein the distal end of the tube is coupled to the distal tip.

9. The delivery device of claim 1, wherein the distal end of the housing or the connector comprises a septum to prevent fluid from flowing into the distal end of the housing.

10. The delivery device of claim 1, wherein the distal end of the tube is closed.

11. The delivery device of claim 1, wherein the distal end of the tube is open.

12. The delivery device of claim 1, wherein the proximal end of the tube is coupled to the elongated core.

13. The delivery device of claim 1, wherein the tube comprises a plurality of openings arranged between the proximal end and the distal end of the tube.

14. The delivery device of claim 13, wherein the openings at the proximal end of the tube are larger than the openings at the distal end of the tube.

15. The delivery device of claim 13, wherein the openings comprise slits arranged perpendicular to a longitudinal axis of the tube.

16. A catheter system, comprising:
a delivery device comprising:
   a housing having a distal end and a proximal end, wherein the distal end of the housing comprises a connector; and
   a fluid-permeable instrument comprising:
      an elongated core having a proximal end and a distal end; and
      a tube having a proximal end and a distal end, the tube at least partially surrounding the elongated core,
wherein the instrument is configured to advance distally from the housing; and
a catheter assembly couplable to the delivery device and comprising:
   a catheter adapter, comprising a distal end, a proximal end, a lumen extending between the distal end and the proximal end; and
   a catheter secured to the catheter adapter and extending distally from the catheter adapter, wherein the catheter comprises a distal end and a proximal end,
wherein the distal end of the tube is configured to be disposed distal to the distal end of the catheter.

17. The system of claim 16, wherein the proximal end of the tube is coupled to the elongated core.

18. The system of claim 16, wherein the tube comprises a plurality of openings arranged between the proximal end and the distal end of the tube.

19. The system of claim 18, wherein the openings at the proximal end of the tube are larger than the openings at the distal end of the tube.

20. The system of claim 18, wherein the openings comprise slits arranged perpendicular to a longitudinal axis of the tube.

* * * * *